(12) United States Patent
Aguirre et al.

(10) Patent No.: US 7,202,489 B2
(45) Date of Patent: Apr. 10, 2007

(54) LED MODIFYING APPARATUS AND METHOD

(75) Inventors: Francis M. Aguirre, St. Paul, MN (US); Michele A. Craton, Cottage Grove, MN (US); Jack W. Lai, Lake Elmo, MN (US); David L. Phillips, White Bear Lake, MN (US); Peter T. Benson, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/869,235

(22) Filed: Jun. 16, 2004

(65) Prior Publication Data

US 2005/0116177 A1    Jun. 2, 2005

Related U.S. Application Data

(63) Continuation-in-part of application No. 10/726,257, filed on Dec. 2, 2003.

(51) Int. Cl.
*G01N 21/00* (2006.01)
*G01N 21/33* (2006.01)
*G02B 6/43* (2006.01)

(52) U.S. Cl. .............. 250/504 R; 250/492.1; 250/461.1

(58) Field of Classification Search .......... 250/492.1, 250/491.1, 504 R, 504 H; 433/29
See application file for complete search history.

(56) References Cited

U.S. PATENT DOCUMENTS

| 4,544,259 A | 10/1985 | Kanaoka et al. |
| 5,140,248 A | 8/1992 | Rowan et al. |
| 5,227,008 A | 7/1993 | Klun et al. |
| 5,299,222 A | 3/1994 | Shannon et al. |
| 5,301,090 A * | 4/1994 | Hed .............................. 362/558 |
| 5,420,768 A | 5/1995 | Kennedy |
| 5,567,032 A | 10/1996 | Heizmann |

(Continued)

FOREIGN PATENT DOCUMENTS

DE    199 23 187 A1    11/2000

(Continued)

OTHER PUBLICATIONS

Article: Hsu, J.T. et al., "Design of multi-chips LED module for lighting application," *Solid State Lighting II, Proceedings of SPIE* (2002), vol. 4776, pp. 26-33.

(Continued)

*Primary Examiner*—Nikita Wells
(74) *Attorney, Agent, or Firm*—Pamela Stewart; Rick Franzen

(57) ABSTRACT

A radiation modifying apparatus comprises a plurality of solid state radiation sources to generate radiation that modifies a first material such as by curing or creating alignment through polarization. The solid state radiation sources can be disposed in an array pattern. Optical concentrators, arranged in a corresponding array pattern, receive radiation from corresponding solid state radiation sources. The concentrated radiation is received by a plurality of optical waveguides, also arranged in a corresponding array pattern. Each optical waveguide includes a first end to receive the radiation and a second end to output the radiation. The radiation modifying apparatus can be utilized for continuous substrate, sheet, piece part, spot curing, and/or 3D radiation-cure processes.

14 Claims, 17 Drawing Sheets

U.S. PATENT DOCUMENTS

| | | | |
|---|---|---|---|
| 5,574,817 A | 11/1996 | Henson et al. | |
| 5,580,471 A | 12/1996 | Fukumoto et al. | |
| 5,611,017 A | 3/1997 | Lee et al. | |
| 5,634,711 A | 6/1997 | Kennedy et al. | |
| 5,713,654 A | 2/1998 | Scifres | |
| 5,808,794 A | 9/1998 | Weber et al. | |
| 5,882,774 A | 3/1999 | Jonza et al. | |
| 5,886,313 A | 3/1999 | Krause et al. | |
| 5,967,653 A | 10/1999 | Miller et al. | |
| 6,045,240 A | 4/2000 | Hochstein | |
| 6,075,595 A * | 6/2000 | Malinen | 356/328 |
| 6,200,134 B1 | 3/2001 | Kovac et al. | |
| 6,224,216 B1 * | 5/2001 | Parker et al. | 353/31 |
| 6,236,382 B1 | 5/2001 | Kawakami et al. | |
| 6,290,382 B1 | 9/2001 | Bourn et al. | |
| 6,395,564 B1 | 5/2002 | Huang | |
| 6,414,801 B1 | 7/2002 | Roller | |
| 6,417,917 B1 * | 7/2002 | Jung et al. | 356/73 |
| 6,541,800 B2 | 4/2003 | Barnett et al. | |
| 6,556,734 B1 * | 4/2003 | Bischel et al. | 385/14 |
| 6,560,038 B1 | 5/2003 | Parkyn, Jr. et al. | |
| 6,603,258 B1 | 8/2003 | Mueller-Mach et al. | |
| 6,608,332 B2 | 8/2003 | Shimizu et al. | |
| 6,614,172 B2 | 9/2003 | Chiu et al. | |
| 6,692,250 B1 * | 2/2004 | Decaudin et al. | 433/29 |
| 6,727,518 B2 | 4/2004 | Uemura et al. | |
| 6,777,870 B2 | 8/2004 | Sundahl | |
| 6,821,143 B2 | 11/2004 | Gasquet et al. | |
| 6,822,190 B2 | 11/2004 | Smithson et al. | |
| 6,874,910 B2 | 4/2005 | Sugimoto et al. | |
| 6,901,090 B1 | 5/2005 | Ohtsuki | |
| 2002/0126479 A1 | 9/2002 | Zhai et al. | |
| 2002/0171047 A1 | 11/2002 | Chan et al. | |
| 2003/0052594 A1 | 3/2003 | Matsui et al. | |
| 2003/0068113 A1 | 4/2003 | Janz et al. | |
| 2003/0091277 A1 | 5/2003 | Mei | |
| 2003/0117691 A1 | 6/2003 | Bi et al. | |
| 2003/0142500 A1 | 7/2003 | Bachl et al. | |
| 2003/0178627 A1 | 9/2003 | Marchl et al. | |
| 2003/0189829 A1 | 10/2003 | Shimizu et al. | |
| 2003/0214571 A1 | 11/2003 | Ishikawa et al. | |
| 2003/0235800 A1 * | 12/2003 | Qadar | 433/29 |
| 2004/0008952 A1 | 1/2004 | Kragl | |
| 2004/0106968 A1 * | 6/2004 | Yamada | 607/88 |
| 2004/0116033 A1 | 6/2004 | Ouderkirk et al. | |
| 2004/0144987 A1 | 7/2004 | Ouderkirk et al. | |
| 2004/0145913 A1 | 7/2004 | Ouderkirk et al. | |
| 2004/0149998 A1 | 8/2004 | Henson et al. | |
| 2004/0164325 A1 | 8/2004 | Siegel | |
| 2004/0166249 A1 | 8/2004 | Siegel | |

FOREIGN PATENT DOCUMENTS

| | | |
|---|---|---|
| DE | 201 11 814 U1 | 12/2001 |
| DE | 201 20 770 U1 | 5/2002 |
| DE | 101 10 835 A1 | 9/2002 |
| DE | 101 34 381 A1 | 1/2003 |
| DE | 101 62 404 A1 | 7/2003 |
| EP | 0 181 193 A | 5/1986 |
| EP | 0 303 741 A1 | 2/1989 |
| EP | 1067332 | 1/2001 |
| EP | 1 108 949 A1 | 6/2001 |
| EP | 1 241 510 A1 | 9/2002 |
| EP | 1 241 869 A | 9/2002 |
| EP | 1 260 196 A2 | 11/2002 |
| JP | 02-142695 | 5/1990 |
| JP | 07240536 A | 9/1995 |
| JP | 2002-065603 A | 3/2002 |
| WO | WO 95/20811 | 8/1995 |
| WO | WO 01/20398 A | 3/2001 |
| WO | WO 01/59360 A1 | 8/2001 |
| WO | WO 02/054129 A1 | 7/2002 |
| WO | WO 02/086972 A1 | 10/2002 |
| WO | WO 03/098387 A2 | 11/2003 |
| WO | WO 2004/081475 A2 | 9/2004 |

OTHER PUBLICATIONS

U.S. Appl. No. 10/670,630, filed Sep. 25, 2003 having title "Lensed Optical Fiber and Method for Making the Same".

U.S. Appl. No. 10/726,225, filed Dec. 2, 2003 having title "Solid State Light Device".

U.S. Appl. No. 10/726,244, filed Dec. 2, 2003 having title "Reflective Light Coupler".

U.S. Appl. No. 10/726,248, filed Dec. 2, 2003 having title "Multiple LED Source and Method for Assembling Same".

U.S. Appl. No. 10/727,220, filed Dec. 2, 2003 having title "Illumination Assembly".

U.S. Appl. No. 10/762,678, filed Jan. 20, 2004 having title "Phosphor Based Light Sources Having Front Illumination".

Book Excerpt: Žukauskas et al., *Introduction to Solid-State Lighting*, John Wiley & Sons, Inc., New York, 2002, pp. 166-167.

"Solid-State Laser/Fiber Optic Expose Machine," IBM Technical Disclosure Bulletin, IBM Corp. vol. 30, No. 10, New York, Sep. 1, 1988, 249-250.

\* cited by examiner

LED MODIFYING APPARATUS AND METHOD

RELATED APPLICATION

The present application is a continuation-in-part of U.S. patent application Ser. No. 10/726,257 filed on Dec. 2, 2003 and entitled "LED Curing Apparatus and Method". The present application is also related to co-owned and concurrently filed U.S. patent application Ser. No. 10/726,225 entitled "Solid State Light Device", incorporated by reference herein in its entirety. The present application is also related to co-owned and concurrently filed U.S. patent applications Ser. No. 10/726,244 entitled "Parabolic Concentrator Light Coupling Device"; Ser. No. 10/726,222 entitled "Illumination System Using a Plurality of Light Sources"; Ser. No. 10/726,248 entitled "White LED Light Source and Method of Assembly"; and Ser. No. 10/727,220 entitled "Flexible Circuit LED Thermal Packaging", each of which is incorporated by reference herein in its entirety.

BACKGROUND OF THE INVENTION

1. Field of the Invention

The present invention relates to a modifying apparatus, system, and method. More particularly, the present invention relates to a solid state light device, system, and method that may replace current high intensity directed light sources and techniques that are used for modification applications.

2. Background Art

Illumination systems are used in a variety of applications. Home, medical, dental, and industrial applications often require light to be made available. Similarly, aircraft, marine, and automotive applications often require high-intensity illumination beams.

Traditional lighting systems have used electrically powered filament or arc lamps, which sometimes include focusing lenses and/or reflective surfaces to direct the produced illumination into a beam. Conventional light sources based on powered filament or arc lamps, such as incandescent or discharge bulbs, radiate both heat and light in 360 degrees. Conventional sources also include microwave-driven sources. Thus, for traditional applications, the optics used must be designed and/or specially treated to withstand the constant heating effects caused by the high intensity (and high heat) discharge bulbs. In addition, expensive and complicated heat transfer systems must be employed if heat is to be removed from the area of illumination.

For example, conventional curing systems utilize water chill rolls to minimize distortion and/or destruction of the substrate and/or the formulation. Other conventional systems utilize a flat water chill plate located just below or in contact with the substrate.

For modifying applications such as curing, stacked-LED arrays are now being investigated (e.g., arrays that can be "stacked" in a cross-machine-direction (CMD) and machine-direction (MD) manner). With these conventional systems, however, the irradiance and lifetime drop quickly as the LED emission wavelengths get shorter. This may lead to problems with initiating chemical reactions via radiation absorption and response by photoinitiators, which are typically formulated to absorb radiation less than 450 nm. If the irradiance is too low, it is possible that the polymerization reaction would not yield desired product properties.

To counteract low irradiance, a conventional technique is to position LEDs close to one another to increase the overall irradiance and attain desired cure. However, arranging the LEDs in such a manner results in several complications relating to thermal management and electrical connections. If the LEDs are more spread out, irradiance uniformity across the array can become non-ideal. Reflectors are sometimes mounted around the LEDs to improve irradiance levels, but this approach still suffers from non-uniformity across the reflector opening. If an appropriate material is not used within the reflector, the irradiance will also drop by the square of the distance to the irradiated surface.

SUMMARY OF THE INVENTION

In accordance with a first embodiment of the present invention, an irradiation apparatus includes a plurality of solid state radiation sources to generate radiation that modifies a first material. A controller is in electrical communication with the solid state radiation sources and causes the solid state radiation sources to generate pulsed radiation. A plurality of optical concentrators are included, and each concentrator receives pulsed radiation from one or more of the plurality of solid state radiation sources. A plurality of optical waveguides are included, and each of the plurality of optical waveguides includes a first end and a second end, and each first end receives pulsed radiation from one or more of the plurality of optical concentrators. A support structure is included to stabilize at least a first portion of the second ends of the plurality of optical waveguides.

In accordance with a second embodiment of the present invention, an irradiation system includes a solid state radiation source that includes a plurality of LED dies to generate radiation that is capable of modifying a radiation modifiable chemical formulation. A controller is electrically connected to the plurality of LED dies and causes the LED dies to produce pulsed radiation. A plurality of optical concentrators are included, and each concentrator receives the pulsed radiation from one or more of the LED dies. A plurality of optical fibers are included, and each of the plurality of optical fibers includes a first end and a second end, and each first end receives concentrated pulsed radiation from one or more of the plurality of optical concentrators. A substrate is included to support the radiation modifiable chemical formulation.

The above summary of the present invention is not intended to describe each illustrated embodiment or every implementation of the present invention. The figures and the detailed description that follow more particularly exemplify these embodiments.

Figure 1:
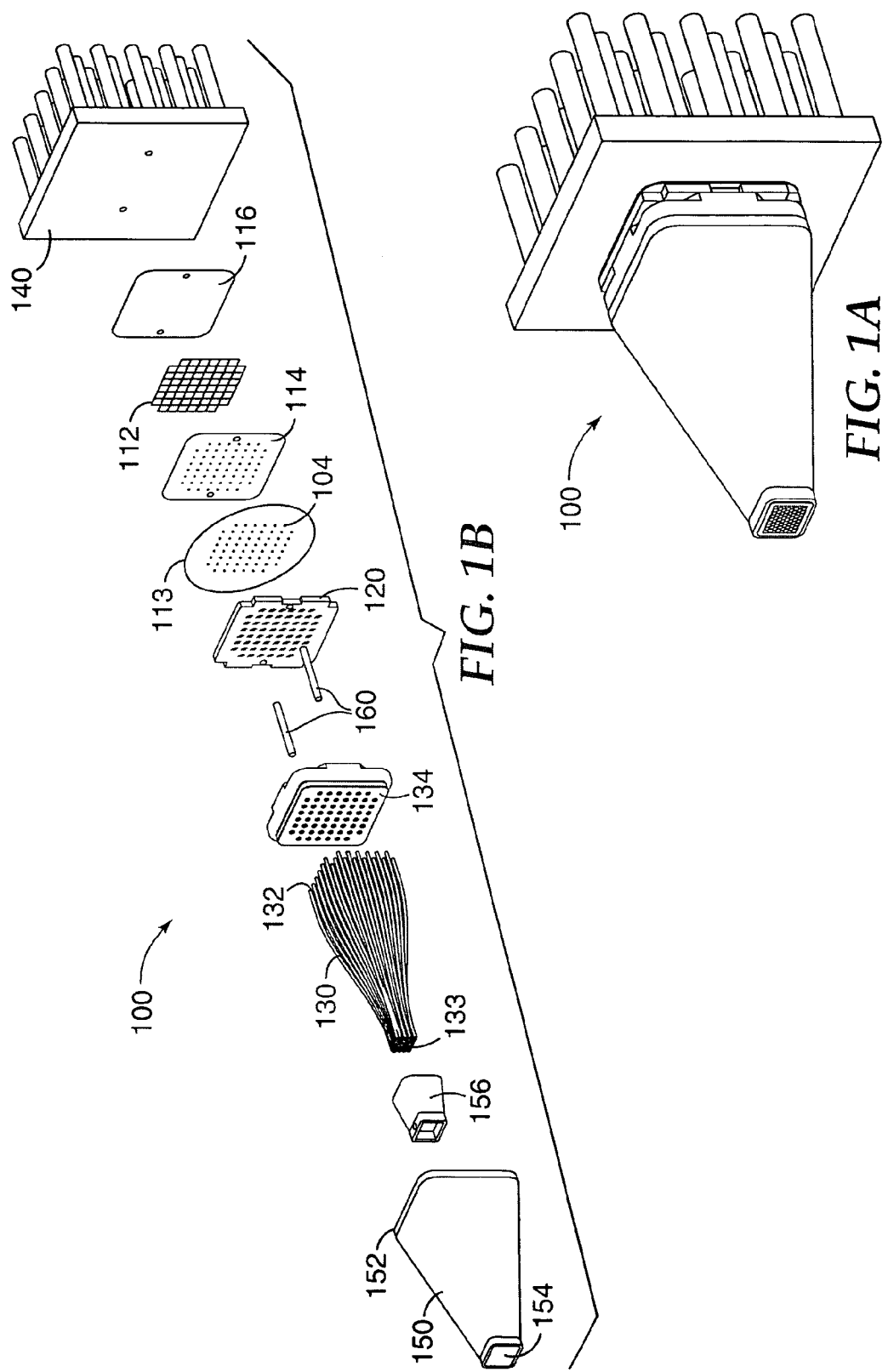
FIG. 1A shows a perspective view and FIG. 1B shows an exploded view of a solid state light device according to an exemplary embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION

FIG. 1A shows a solid state light device 100 (also referred to herein as an illumination device or photon emitting device) in an exemplary configuration. Light device 100 is shown in an exploded view in FIG. 1B. By "light" it is meant electromagnetic radiation having a wavelength in the ultraviolet, visible, and/or infrared portion of the electromagnetic spectrum. In the construction described below, the light device 100 can have an overall compact size comparable to that of a conventional High Intensity Discharge (HID) bulb, thus providing a replacement for a lamp device in various applications including road illumination, spot lighting, back lighting, image projection and radiation activated curing.

Light device 100 comprises an array of solid state radiation sources 104 to generate radiation. The radiation is collected and concentrated by a corresponding array of optical concentrators 120. The concentrated radiation is then launched into a corresponding array of waveguides 130, which are supported by a support structure 150. Each of these features will now be described in more detail.

In an exemplary embodiment, the solid state radiation sources 104 comprise a plurality of discrete LED dies or chips disposed in an array pattern, however other solid state radiation sources are applicable as well including laser diodes. The discrete LED dies 104 are mounted individually and have independent electrical connections for operational control (rather than an LED array where all the LEDs are connected to each other by their common semiconductor substrate). LED dies can produce a symmetrical radiation pattern and are efficient at converting electrical energy to light. As many LED dies are not overly temperature sensitive, the LED dies may operate adequately with only a modest heat sink compared to many types of laser diodes. In an exemplary embodiment, each LED die is spaced apart from its nearest neighbor(s) by at least a distance greater than an LED die width. In a further exemplary embodiment, each LED die is spaced apart from its nearest neighbor(s) by at least a distance greater than six LED die widths. These exemplary embodiments provide for suitable thermal management, as explained in further detail below.

In addition, LED dies 104 can be operated at a temperature from −40° to 125° C. and can have operating lifetimes in the range of 100,000 hours, as compared to most laser diode lifetimes around 10,000 hours or UV arc lamp lifetimes of approximately 2,000 hours. In an exemplary embodiment, the LED dies can each have an output intensity of about 50 Lumens or more. Discrete high-power LED dies can be GaN-based LED dies commercially available from companies such as Cree (such as Cree's InGaN-based XBright™ products) and Osram. In one exemplary embodiment, an array of LED dies (manufactured by Cree), each having an emitting area of about 300 µm×300 µm, can be used to provide a concentrated (small area, high power) light source. Other light emitting surface shapes such as rectangular or other polygonal shapes can also be utilized. In addition, in alternative embodiments, the emission layer of the LED dies utilized can be located on the top or bottom surface.

In some exemplary embodiments, a plurality of barely blue or ultraviolet (UV) LED dies can be utilized. In alternative embodiments, one or more LED dies can be coated, preferably on a light-emitting surface, with a phosphor layer (not shown), such as YAG:Ce phosphor for the blue LED die, or a mixture of RGB (red, green, blue) phosphors utilized with a UV LED die. Thus, the phosphor layer can be used to convert the output of the LED die into "white" light under different mechanisms. Phosphor layer placement and construction is described in detail in a co-owned and concurrently filed application entitled "Illumination System Using a Plurality of Light Sources", incorporated by reference above.

In an alternative embodiment, a collection of red, blue, and green LED dies can be selectively placed in an array. The resulting emission is collected by the array of fibers 130 so that the light emitted from the output ends of the fibers is seen by an observer as colored light or "white" light, when blended together in concert.

In an alternative embodiment, the LED die array may be replaced with a vertical cavity surface emitting laser (VCSEL) array, which can conventionally provide output in the visible region, including "white" light.

As shown in FIG. 1B, the emission from LED dies 104 is received by a plurality of optical concentrators 120 which are disposed in a corresponding array pattern. In an exemplary embodiment, each optical concentrator receives radiation from a corresponding one of the LED dies 104. In an exemplary embodiment, the optical concentrators 120 comprise non-imaging optical concentrators (also referred to as reflective optical couplers) disposed in an array. The shape of the reflective surfaces of the optical concentrators 120 are designed to capture a substantial portion of the radiation emitted by each of the sources 104 to preserve the power density. In addition, the concentrated output can be designed in a manner to substantially match the acceptance angle criteria of the light receiving waveguides, so that a substantial portion of the radiation is usably captured by the waveguides 130 and guided therethrough. In an exemplary embodiment, each non-imaging concentrator of the array of non-imaging concentrators 120 has an interior reflecting surface conforming to a two-dimensional (2-D) surface, with at least a second portion of the interior reflecting surface conforming to a three-dimensional (3-D) surface. This and other reflective surface designs are described in detail in the commonly owned and co-pending patent application entitled "Reflective Light Coupler", filed concurrently, and incorporated by reference herein in its entirety.

Each optical concentrator in array 120 can be formed by, e.g., injection molding, transfer molding, microreplication, stamping, punching or thermoforming. The substrate or sheeting in which the optical concentrators 120 can be formed (singularly or as part of an array of optical concentrators) can include a variety of materials such as metal, plastic, thermoplastic material, or multilayer optical film (MOF) (such as Enhanced Specular Reflector (ESR) film available from 3M Company, St. Paul, Minn.). The substrate material used to form the optical concentrator 120 can be coated with a reflective coating, such as silver, aluminum, or reflective multilayer stacks of inorganic thin films, or simply polished in order to increase its reflectivity.

In addition, the optical concentrator substrate can be disposed so that the array of optical concentrators can be oriented beneath, around, or above the LED dies. In an exemplary embodiment, the optical concentrator substrate is disposed on or proximate to the LED array so that each concentrator of array 120 can be formed to slide over each LED die 104, so that the optical concentrator's lower opening 123 (see FIG. 4) provides a close fit around the perimeter of the LED die 104. Alternative concentrator designs include the additional use of a reflective coating on the substrate on which the LED die is supported.

An aspect of the illustrated embodiment of FIG. 1B is the one-to-one correspondence between each radiation source, a corresponding optical concentrator, and a corresponding waveguide. Each optical concentrator surface is designed to convert the isotropic emission from a corresponding LED die, which can be a phosphor-coated LED die in some applications, into a beam that will meet the acceptance angle criteria of a corresponding light-receiving waveguide. As stated above, this concentrator surface design aids in preserving the power density of the light emitted from the LED dies.

Referring back to FIG. 1B, the concentrated output radiation is received by a plurality of optical waveguides 130, shown in FIG. 1B as an array of optical fibers, with each waveguide having an input end 132 and an output end 133. The present exemplary embodiment includes an array 130 of large-core (for example, 400 µm to 1000 µm) polymer clad silica fibers (such as those marketed under the trade designation TECS™, available from 3M Company, St. Paul, Minn.). In a further exemplary embodiment, each of the optical fibers 130 can comprise polymer clad silica fibers having a core diameter of about 600 µm to 650 µm. In exemplary embodiments, the longitudinal lengths of the fibers can be about 1 to 5 inches (2.5 cm–12.5 cm) in length. As the exemplary fibers are very flexible, this short distance still provides the ability to place the fibers in a tight, patterned bundle at the output ends. In addition, the short length provides for a very compact device having a size comparable to the size of conventional HID lamps. Of course, the fiber lengths can be increased in other applications without causing a detrimental effect in output.

Other types of optical fibers, such as conventional or specialized silica fibers may also be utilized in accordance with the embodiments of the present invention, depending on such parameters as, e.g., the output wavelength(s) of the LED die sources. For example, polymeric fibers may be susceptible to solarization and/or bleaching with applications involving deep blue or UV light sources. In the present exemplary embodiments, based on the type of photo-initiator or other curable material to be irradiated, optical fibers/waveguides that provide low losses for wavelengths of 450 nm or less can be utilized.

Alternatively, as would be apparent to one of ordinary skill given the present description, other waveguide types, such as planar waveguides, polymer waveguides, flexible polymer waveguides, or the like, may also be utilized in accordance with the present teachings.

Once the light emitted by the LED die is collected and redirected by the concentrator into the light-receiving fiber, the fiber(s) can be used to transport the light to a specific location with low optical loss by total internal reflection. However, the light receiving fibers do not only serve to transport light—by translating the fibers from the wider spacing of the LED die array to a tighter spacing or spacings at the output aperture, such as a tight packed fiber bundle, light from the (relatively) dispersed LED array can be effectively concentrated into a very small area. Also, the optical design of the exemplary light receiving fiber core and cladding provide for shaping the light beams emerging from the bundled ends due to the Numerical Aperture (NA) of the fibers at the input end as well as the output end. As described herein, the light receiving fibers perform light concentrating and beam shaping, as well as light transportation.

The optical fibers 132 may further include fiber lenses on one or more of the output ends 133 of the optical fibers. Similarly, the light receiving ends 132 of the optical fibers 130 may each further comprise a fiber lens. Fiber lens manufacture and implementation is described in commonly owned and co-pending U.S. patent application Ser. Nos. 10/317,734 and 10/670,630, incorporated by reference herein. Alternatively, optical element(s), such as a lens, lenslets, mirror, or polarizer, can be placed adjacent the second end(s) of the fiber(s) to focus, diffuse, collimate, or polarize the irradiance. An optical element may be continuous across multiple fibers or may be discrete.

A fiber array connector 134 can be utilized to support the first ends of each optical fiber of array 130. In an exemplary embodiment, the fiber array connector 134 comprises a rigid material, such as a molded plastic material, with a plurality of apertures having a pattern corresponding to the pattern of optical concentrators 120. Each aperture receives the input end 132 of an optical fiber of array 130 and can provide for straightforward bonding thereto.

In an exemplary embodiment, an interconnect circuit layer, rigid or flexible, can be utilized to provide thermal management for and electrical connection to the LED dies 104. As shown in FIG. 1B, the interconnect circuit layer can comprise a multilayer structure, such as 3M™ Flexible (or Flex) Circuits, available from 3M Company, Saint Paul, Minn. For example, the multilayer interconnect layer can comprise a metal mounting substrate 112, made of e.g., copper or other thermally conductive material, an electrically insulative dielectric layer 114, and a patterned conductive layer 113, where the LED dies are operatively connected to bond pads (not shown) of the conductive layer 113. Electrically insulative dielectric layer 114 may comprise of a variety of suitable materials, including polyimide, polyester, polyethyleneterephthalate (PET), polycarbonate, polysulfone, or FR4 epoxy composite, for example. Electrically and thermally conductive layer 113 may comprise of a variety of suitable materials, including copper, nickel, gold, aluminum, tin, lead, and combinations thereof, for example.

In an exemplary embodiment, and as described in more detail below, one or more groups of the LED dies 104 are interconnected with each other, but separate from other groupings of LED dies, to provide for pixilated radiation output. Vias (not shown) can be used to extend through the dielectric layer 114. The metal mounting substrate 112 can be mounted on a heat sink or heat dissipation assembly 140. The substrate 112 can be separated from heat sink 140 by a layer 116 of electrically insulative and thermally conductive material. In an exemplary embodiment, heat sink 140 can further comprise a series of thermal conductor pins to further draw heat away from the LED die array during operation.

In one exemplary embodiment, each bare LED die 104 can reside in a recessed portion of the dielectric surface 114, directly on the metal/circuit layer 113. Example implementations of interconnect circuitry are described in a currently pending and co-owned application entitled "Flexible Circuit LED Thermal Packaging", incorporated by reference herein in its entirety.

In another embodiment, a more rigid FR4 epoxy based printed wiring board structure can be utilized for electrical interconnection. In yet another embodiment, a low cost circuit can be prepared by patterning conductive epoxy or conductive ink onto a suitable substrate as required to connect the LED die array.

Solid state light device 100 further includes a support structure. In the exemplary embodiment of FIG. 1B, the support structure is configured as a housing 150, having an input aperture 152 and an output aperture 154. The housing 150 provides strain relief for the array of waveguides 130 and can prevent damage to the waveguides 130 from outside sources. In addition, housing 150 can provide a rigid support that is preferred for vehicular applications, such as those described in more detail below. Optionally, when waveguides 130 are optical fibers, the support structure can further include a banding 156 that is disposed in contact with a perimeter portion of the second ends of waveguides 130. The banding 156 can aid in distributing the output ends 134 of waveguides 130 in a selected output pattern, as is described in further detail below.

In addition, the fiber array connector 134 can include a ridge or indentation to receive the input aperture 152 of housing 150. While the housing 150 may be bonded or otherwise attached to fiber array connector 134, in an exemplary embodiment, the housing 150 is snap fit on fiber array connector 134.

In an exemplary construction method, the fibers are first loaded into the fiber array connector and bonded to the connector. A fixture (not shown) can be utilized to group fibers in rows to have an ordered grouping. The fixture can comprise multiple partitions that repeatably position each fiber from the input end to the output end. In addition, the fixture can be designed so that the fibers do not cross over one another and have a predictable location for the output ends. To secure the output end, a rigid or flexible banding, e.g. a polymer material, is utilized to fix the location of the fibers within a desired output pattern. The strain relief/support housing can then be slid over the fibers and banding and secured to the fiber array connector. The banding can be secured within the output aperture of the housing through the use of conventional adhesives or bonding elements. Alternatively, the support structure can comprise an encapsulate material that is formed throughout and around the fiber bundle(s).

Alternatively, support structure 150 can comprise an adhesive material, such as a binding epoxy, which can be applied to a portion of the waveguides 130, such that when the adhesive sets, the waveguides are fixed in a desired pattern.

Overall alignment can be provided by one or more alignment pins 160, which can be used to align the fiber array connector 134, concentrator array 120, interconnect circuit layer 110 and heat sink 140 together. A series of alignment holes, such as alignment holes 162 shown in FIG. 2, can be formed in each of the aforementioned parts of the device 100 to receive the alignment pins 160. Alignment of the optical concentrator array 120 to the interconnect circuit layer can be accomplished through the use of fiducials (not shown).

Figure 2:
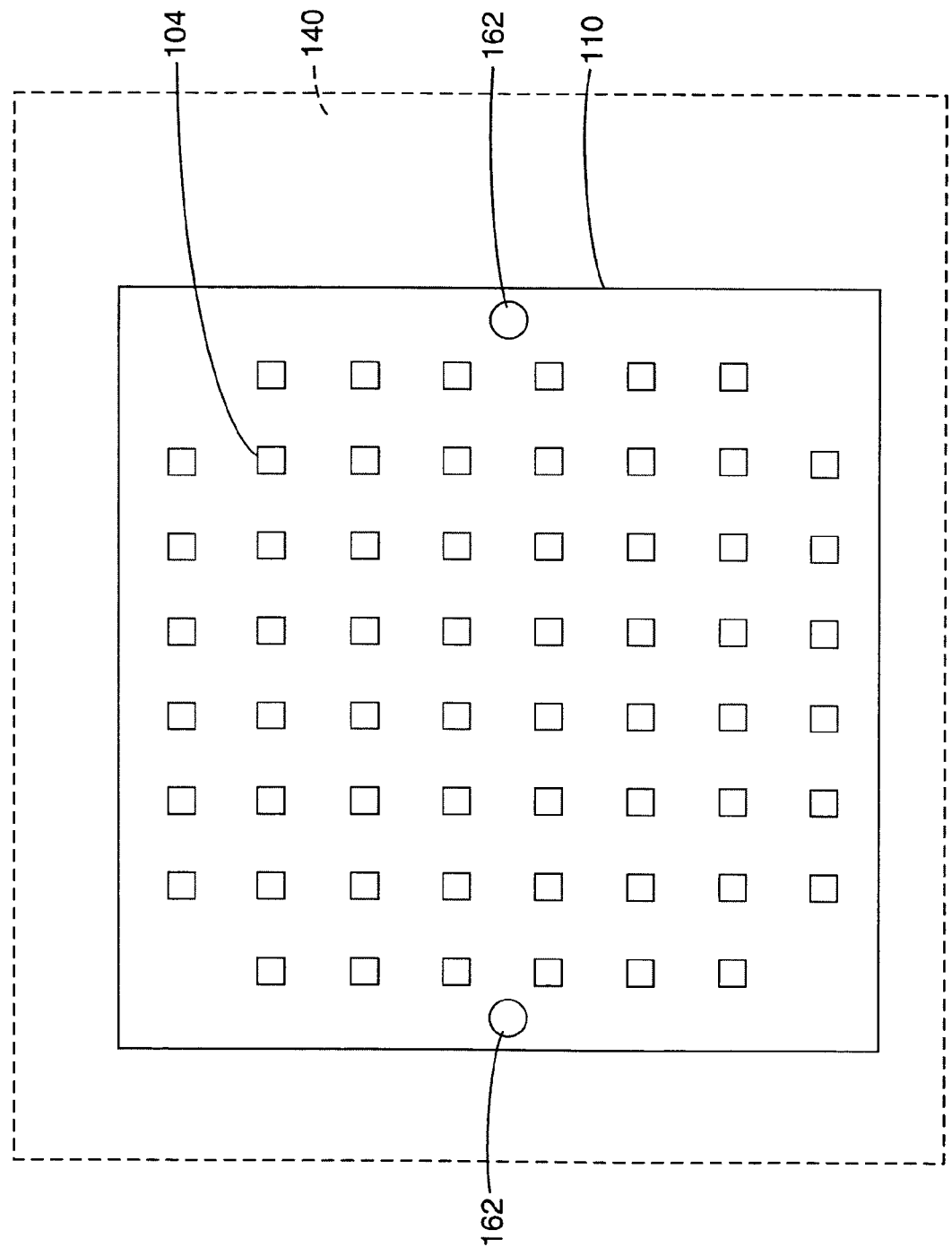
FIG. 2 shows a top view of an exemplary LED die array disposed on an interconnect circuit according to an embodiment of the present invention.

FIG. 2 illustrates the footprint of the solid state light device 100. In this exemplary configuration, an array of sixty (60) LED dies 104 can be provided on an interconnect circuit layer 110, which is mounted on heat sink 140, in a substantially rectangular array pattern. Of course, in accordance with the present invention, the array of LED dies can comprise a substantially greater or lesser number of LED dies 104. However, as each LED die has a width of about 300 micrometers, and each LED die 104 can be spaced from its nearest neighbor by more than a LED die width, the solid state light source of the present invention can provide a high overall power density, a compact footprint area (about 1 $in^2$ to 4 $in^2$, or 6.5 cm to 26 $cm^2$) and adequate thermal control. In addition, the footprint of the output ends of the fibers 133 (see FIG. 1B) can be even more compact, for example, on the order of about 0.1 $in^2$ to 1 $in^2$ (0.65 $cm^2$ to 6.5 $cm^2$), in exemplary embodiments. Alternatively, the footprint of the output ends may be much longer in one direction over another, such as is shown in one or more of the embodiments described below.

Figure 3:
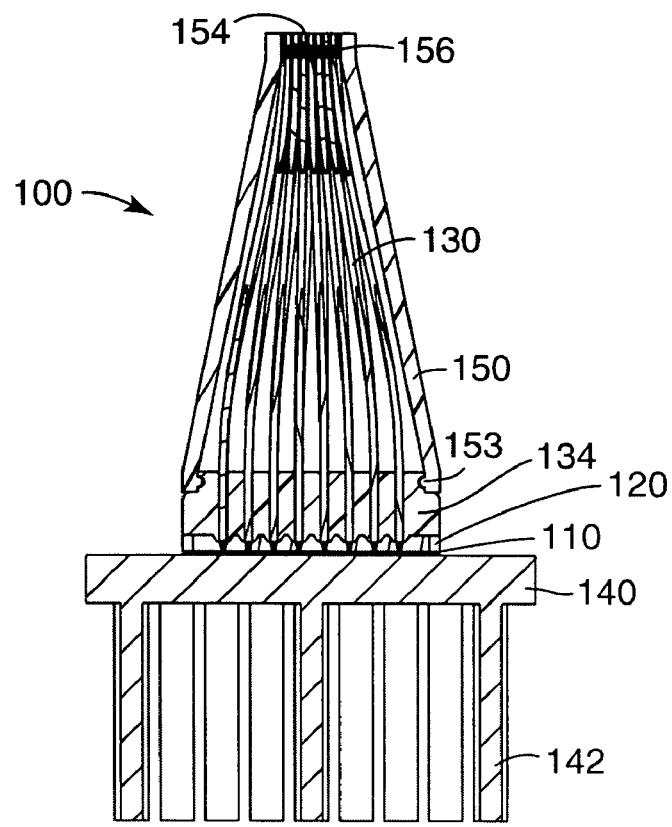
FIG. 3 shows a side view of a solid state light source according to an embodiment of the present invention.

A side view of solid state light device 100 is shown in FIG. 3. In this exemplary embodiment, interconnect circuit layer 110 (having LED dies mounted thereon) is disposed on heat sink 140, which further includes heat dissipation pins 142 that extend in an opposite direction from the output aperture 154. In addition, as described above, the housing 150 can include protrusions 153 to allow for snap fitting onto fiber array connector 134. The array of optical concentrators 120 is disposed between the fiber array connector 134 and the interconnect layer 110. In this embodiment, fibers 130 are supported by the fiber array connector 134 and the banding 156, which is disposed within the output aperture 154 of housing 150.

Figure 4:
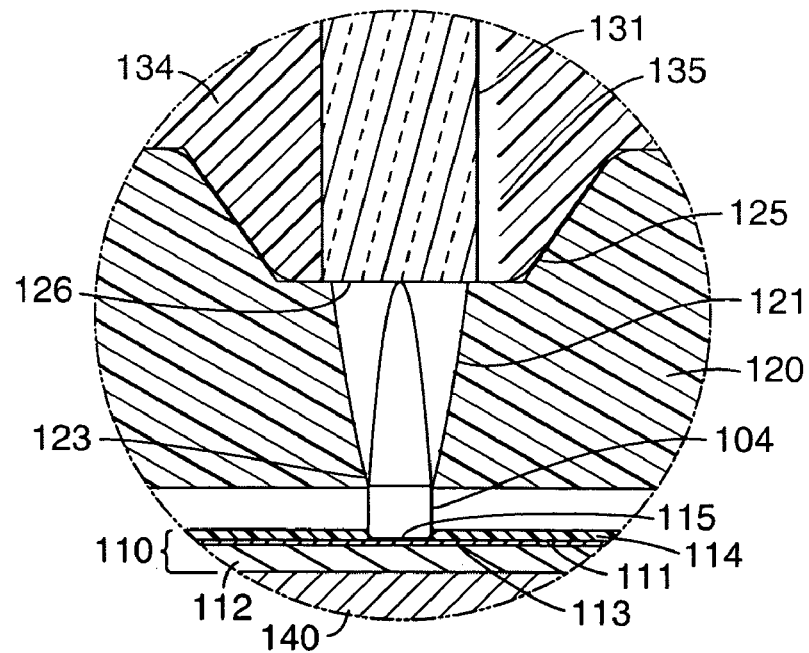
FIG. 4 shows a close-up view of an individual LED die coupled to an optical fiber by a non-imaging optical concentrator according to an embodiment of the present invention.

As shown in greater detail in FIG. 4, an exemplary construction of the solid state light device includes a fiber-concentrator alignment mechanism that reduces misalignment between an individual optical fiber 131 of the fiber array and an individual optical concentrator 121 of the concentrator array. In particular, the fiber array connector 134 can further include a protrusion portion 135 that engages in a depression portion 125 of the optical concentrator array substrate. Thus, fiber 131 is received in an aperture of the fiber array connector 134. The fiber array connector is then disposed on the optical concentrator substrate such that protrusion 135 is received by depression 125. In this manner, the output aperture 126 of optical concentrator 121 can be substantially flush with the input end of fiber 131. In addition, with this exemplary design, multiple input ends of the fibers can be polished at the same time so that the fiber ends are positioned with respect to the optical concentrators.

In the example construction of FIG. 4, the receiving aperture 123 of optical concentrator 121 can be disposed to be proximate to or to surround the perimeter of an emission surface of a corresponding LED die 104. Although not shown, spacers located between the optical concentrator substrate and the interconnect circuit layer can set the proper spacing between these two components. The optical concentrator substrate can then be affixed to the spacers or otherwise bonded to the interconnect circuit layer using conventional techniques.

FIG. 4 further shows a cross section of an exemplary multiple layer interconnect 110, which comprises a conductive epoxy 115 to bond LED die 104 to interconnect layer 110. First and second electrically conductive layers 113, 111 (that can comprise, e.g., nickel and gold, or other conductive materials), provide electrical traces to each LED die in the array, with dielectric layer 114 (e.g., polyimide) disposed to provide electrical insulation. A substrate 112 (e.g., copper) is provided to support the conductive and insulating layers, as well as to provide thermal conductivity to the heat sink 140 to conduct heat away from the direction of emission.

Figure 5A:
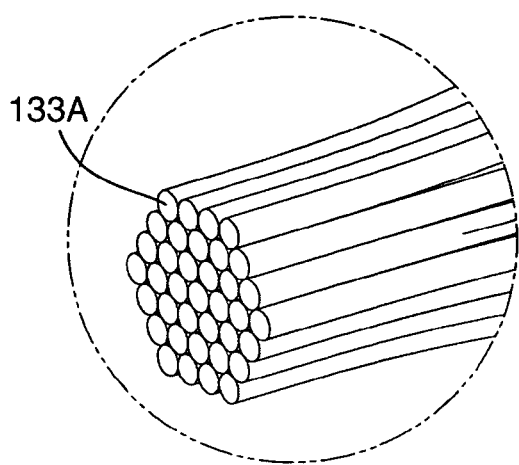
FIGS. 5A–5F show alternative fiber output patterns according to alternative embodiments of the present invention.
Figure 5B:
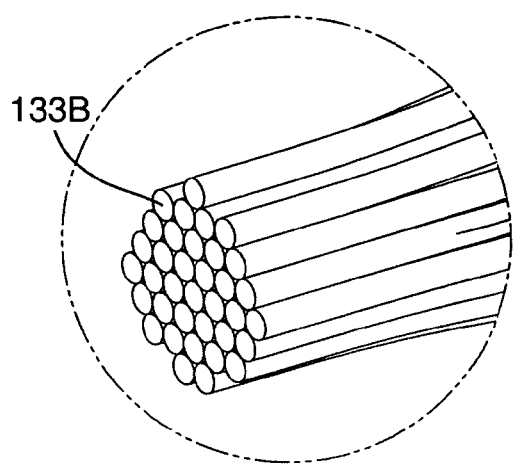
Figure 5C:
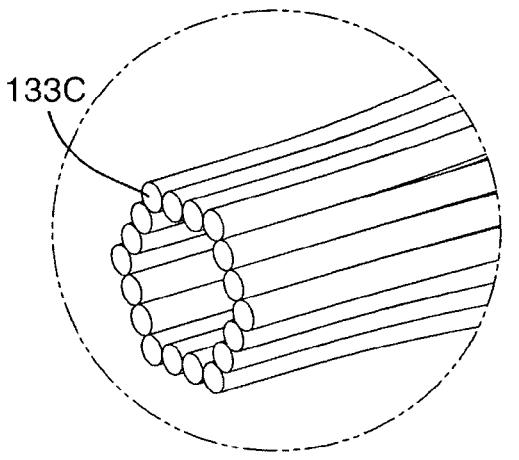
Figure 5D:
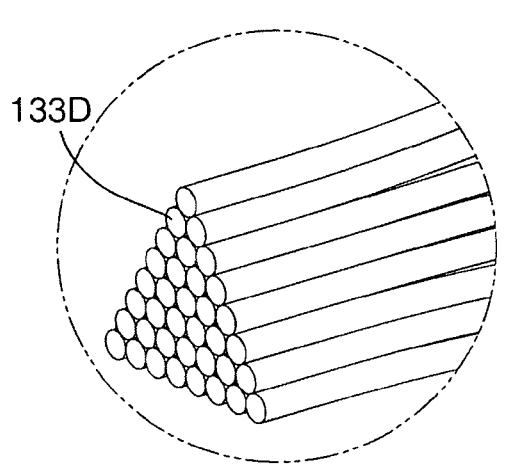
Figure 5E:
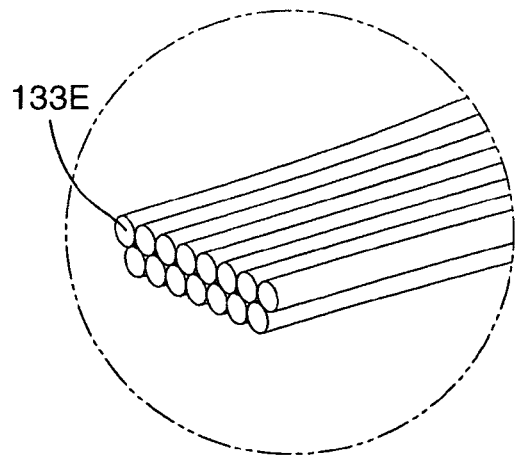
Figure 5F:
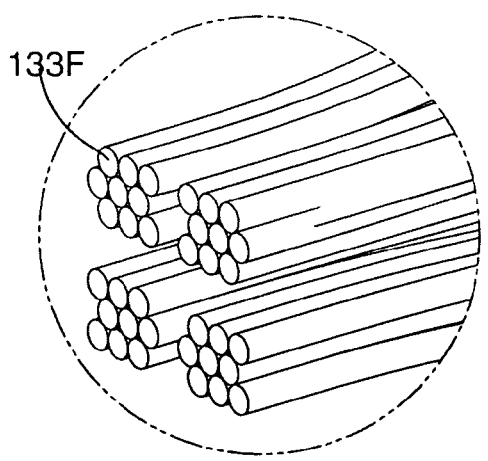

In accordance with the principles described herein, the solid state light device can provide a highly directional and/or shaped output emission, in one or more directions simultaneously. As shown in FIGS. 1A and 1B, the output ends 133 of fiber array 130 can be patterned to provide a rectangular or square output. FIGS. 5A–5F illustrate alternative reconfigurable output end patterns for the fiber array that can be employed depending on the type of illumination that is required for a particular application. For example, FIG. 5A shows a hexagonal output fiber pattern 133A, FIG. 5B shows a circular output fiber pattern 133B, FIG. 5C shows a ring-shaped output fiber pattern 133C, FIG. 5D shows a triangular output fiber pattern 133D, and FIG. 5E shows a line-shaped output fiber pattern 133E. In addition, as shown in FIG. 5F, in an alternative exemplary embodiment, a segmented output pattern 133F can be provided, where multiple separate fiber output groupings can be utilized for specific targeted illumination. As the banding that secures the output ends of the fibers can be formed from a material with flexibility, such as lead, tin, and zinc-based materials and alloys, in some applications, the fiber output pattern can be reconfigurable.

Figure 6A:
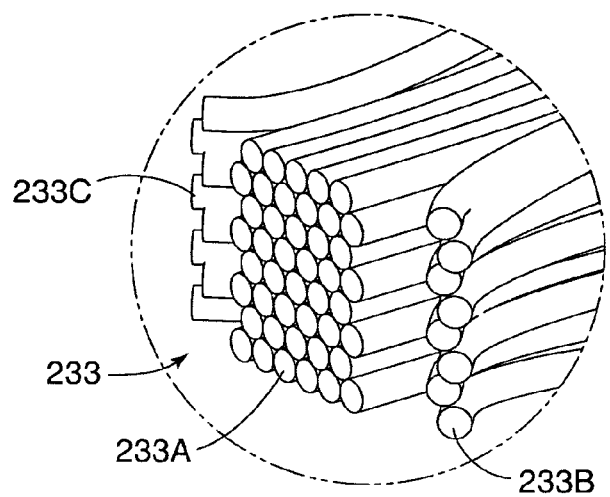
FIG. 6A shows an alternative fiber output pattern for a steerable output and FIGS. 6B and 6C respectively show exemplary banding and support structure implementations for a steerable output in accordance with alternative embodiments of the present invention.
Figure 6B:
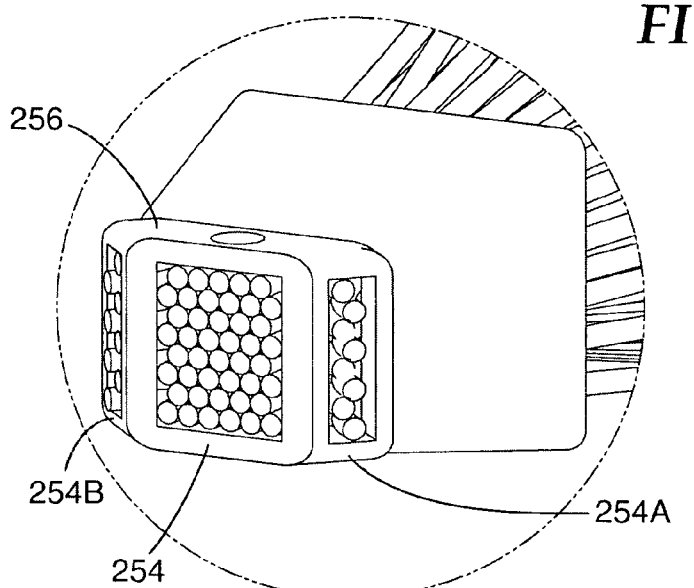
Figure 6C:
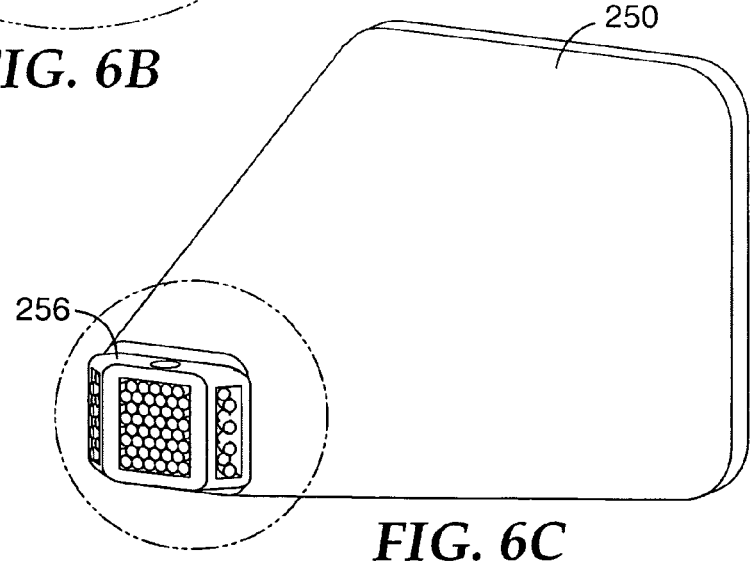

As shown in FIGS. 6A–6C, the output of the solid state light device can be steerable, so that one or more different directions can be illuminated simultaneously or alternatively. FIG. 6A shows fiber output ends 233 arranged, e.g., in three different groupings, 233A, 233B, and 233C. For example, the solid state light device can provide output illumination in a forward direction through output ends 233A under normal operation. In the event of a trigger signal, the LED dies that correspond to the output fibers 233B can be activated so that additional illumination can be provided in that side direction through output fibers 233B. Similarly, the LED dies which correspond to the output fibers 233C can be activated so that additional illumination can be provided in that other side direction.

In curing applications, such as described below with respect to FIG. 12, the "steering" of the fiber output can facilitate radiation curing of complex three-dimensional parts and structures. These types of structures are not well suited for "flood"-type curing with conventional sources, as shadowing effects result in non-uniform curing. In addition, conventional arrays of packaged LEDs arranged on rigid circuit boards are not easily bent to accommodate complex shapes.

Alternatively, a steerable illumination system can be provided utilizing a laterally extended output arrangement of fibers, such as shown in FIG. 5E, whereby the pixilation control circuitry described below (see e.g., FIGS. 9A and 9B) can activate blocks of illuminated fibers from one side to the other. In this manner, the output illumination can be directed towards (or away from) a particular direction, depending on the application.

In this manner, a non-mechanical approach can be used to provide steerable output illumination from the solid state light device. Alternatively, as would be apparent to one of ordinary skill in the art given the present description, greater or fewer fiber groupings can be utilized. In addition, the groupings can have a different relative orientation.

In FIG. 6B, a construction is shown that can be utilized to stabilize and support the different fiber groupings. For example, a banding 256 is provided at the output ends of the optical fibers. The banding 256 can provide a first aperture 254, a second aperture 254A and a third aperture 254B, where the fibers disposed in apertures 254A and 254B will output light in different directions from the fibers disposed in aperture 254. In addition, as shown in FIG. 6C, the banding 256 can be connected to or integral with housing 250, as part of the support structure for the solid state light device.

Figure 7:
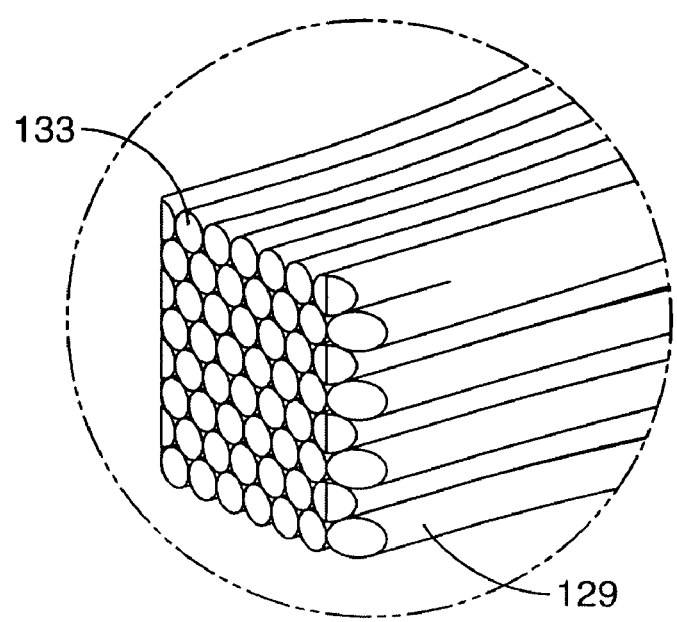
FIG. 7 shows another alternative output pattern for a steerable output, where a portion of the output ends of the fibers have angle polished output faces in accordance with an alternative embodiment of the present invention.

Alternatively, as shown in FIG. 7, the solid state light device can generate steerable light from a single bundle of fiber output ends. For example, fiber output ends 133 can be provided in the same location, such as output aperture 254 from FIG. 6B. In this exemplary embodiment, a portion of these output ends, identified as fiber output ends 129, are angle polished at a different angle, or even substantially different angle (e.g., by 10 to 50 degrees with respect to the fiber axis), than the remainder of fiber output ends 133. The resulting emission will be directed in a different direction from that of the output of fiber ends 133. Thus, similar to the application discussed above with respect to FIGS. 6A–6C, the solid state light device can provide output illumination in a both a forward direction (through output ends 133) and a side direction (through output fibers 129).

Figure 13:
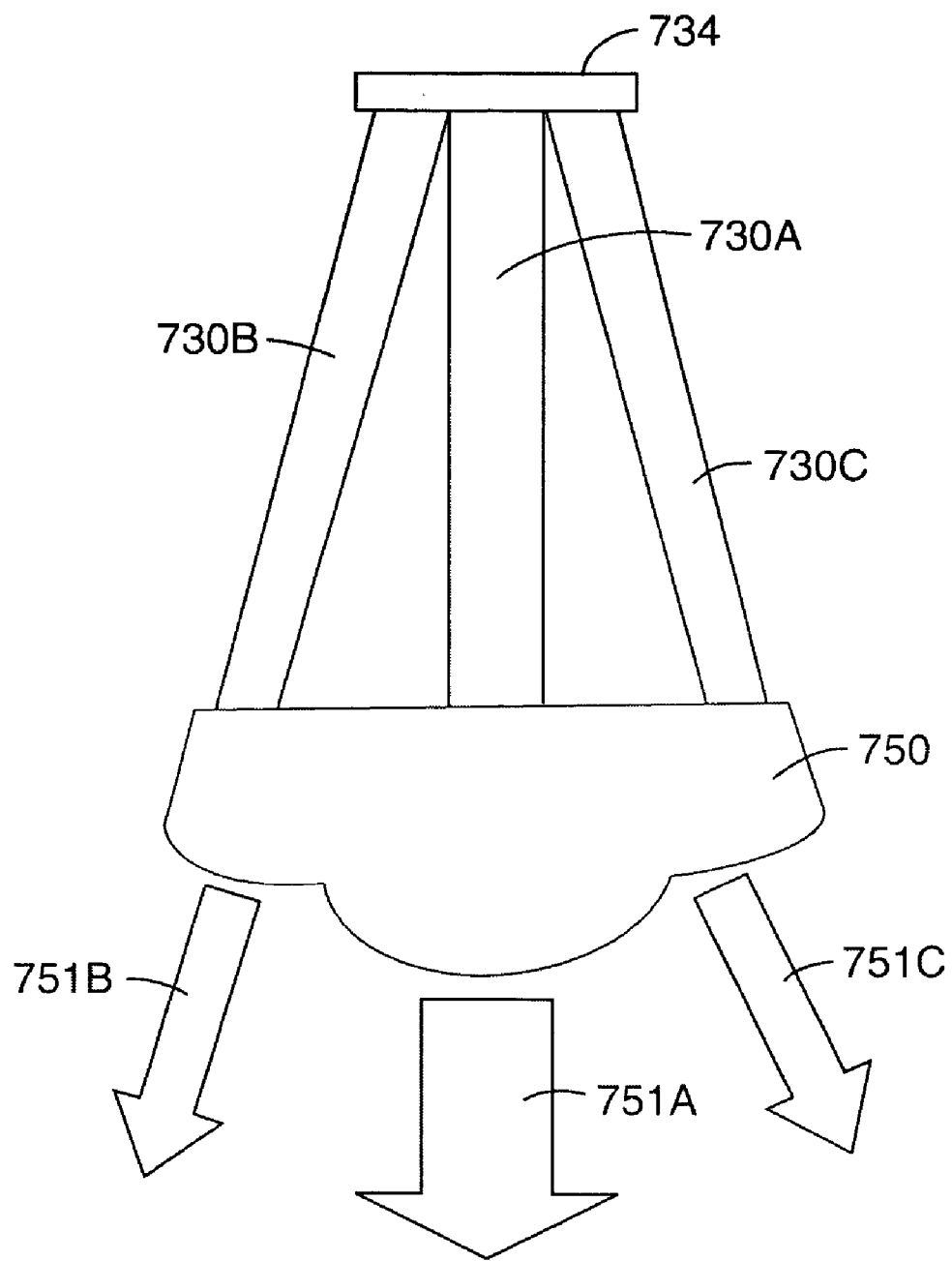
FIG. 13 shows an alternative embodiment for a steerable output emission.

In an alternative embodiment to provide steerable illumination, illustrated in FIG. 13, fibers extending from fiber array connector 734 can be bundled into multiple offset fiber bundles, central bundle 730A and side bundles 730B and 730C. Light emitted by the output ends of the fiber bundles is received by a multi-focus lens 750, such as an aspheric lens, that further directs the output from the offset bundles into desired different illumination regions 751A, 751B, and 751C.

Figure 8:
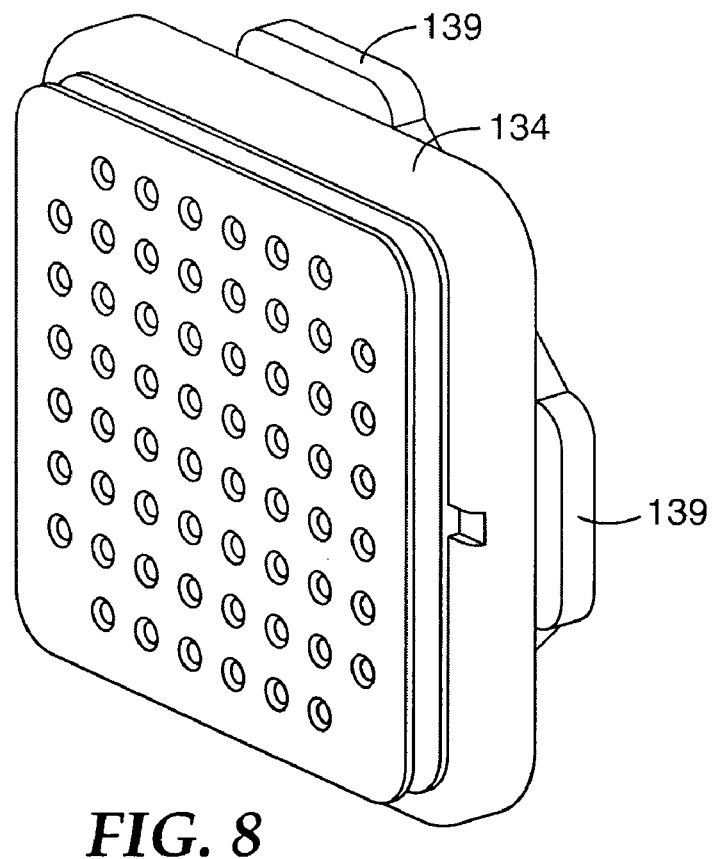
FIG. 8 shows an alternative construction for a fiber array connector in accordance with an embodiment of the present invention.

In an exemplary embodiment of the present invention, the solid state light device can be utilized as a bulb replacement for a discharge-type illumination source. For example, attachment to an existing receptacle can be accomplished through the use of flanges 139, shown in FIG. 8. Flanges 139 can be disposed on the perimeter portion of e.g., the fiber array connector 134. The flange can be designed to engage in a locking slot of such a receptacle. Alternatively, the flanges may be formed on other components of the solid state light device, such as the housing or optical concentrator substrate.

Figure 9A:
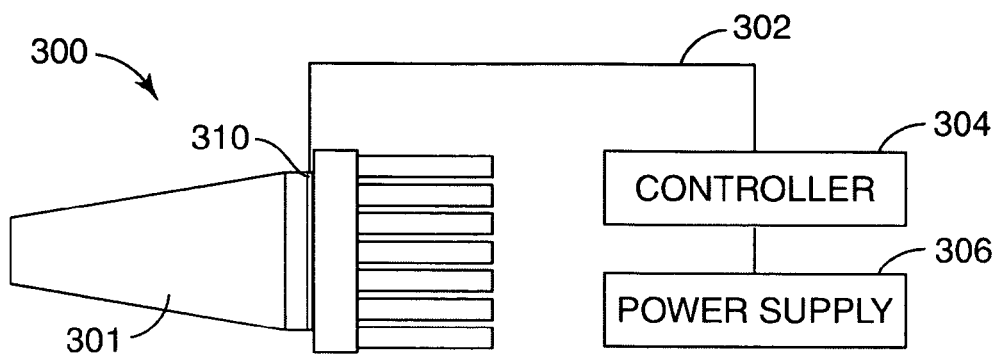
FIG. 9A shows a solid state lighting system adapted for pixilation in accordance with another embodiment of the present invention.

According to another embodiment of the present invention, as shown in FIG. 9A, an illumination system 300 is provided that allows for pixilated light control that can be used for aperture shaping and/or dynamic beam movement. System 300 includes a solid state light source 301 that is constructed in a manner similar to solid state light source 100 described above. A controller 304 is coupled to solid state light source 301 via wiring 302 and connector 310, which can be connected to the interconnect circuit layer. A power source 306 is coupled to the controller 304 to provide power/current to the solid state light source 301.

In an exemplary embodiment, controller 304 is configured to selectively activate individual LED dies or groups of LED dies that are contained in solid state light source 301. In addition, as the light receiving waveguides are provided in a one to one correspondence with the LED dies, the illumination system 300 can provide a pixilated output. This type of pixilated control allows for the control of differently colored (e.g., red, green, and blue for RGB output) or similarly colored (e.g., white, blue, UV) LED dies.

Figure 9B:
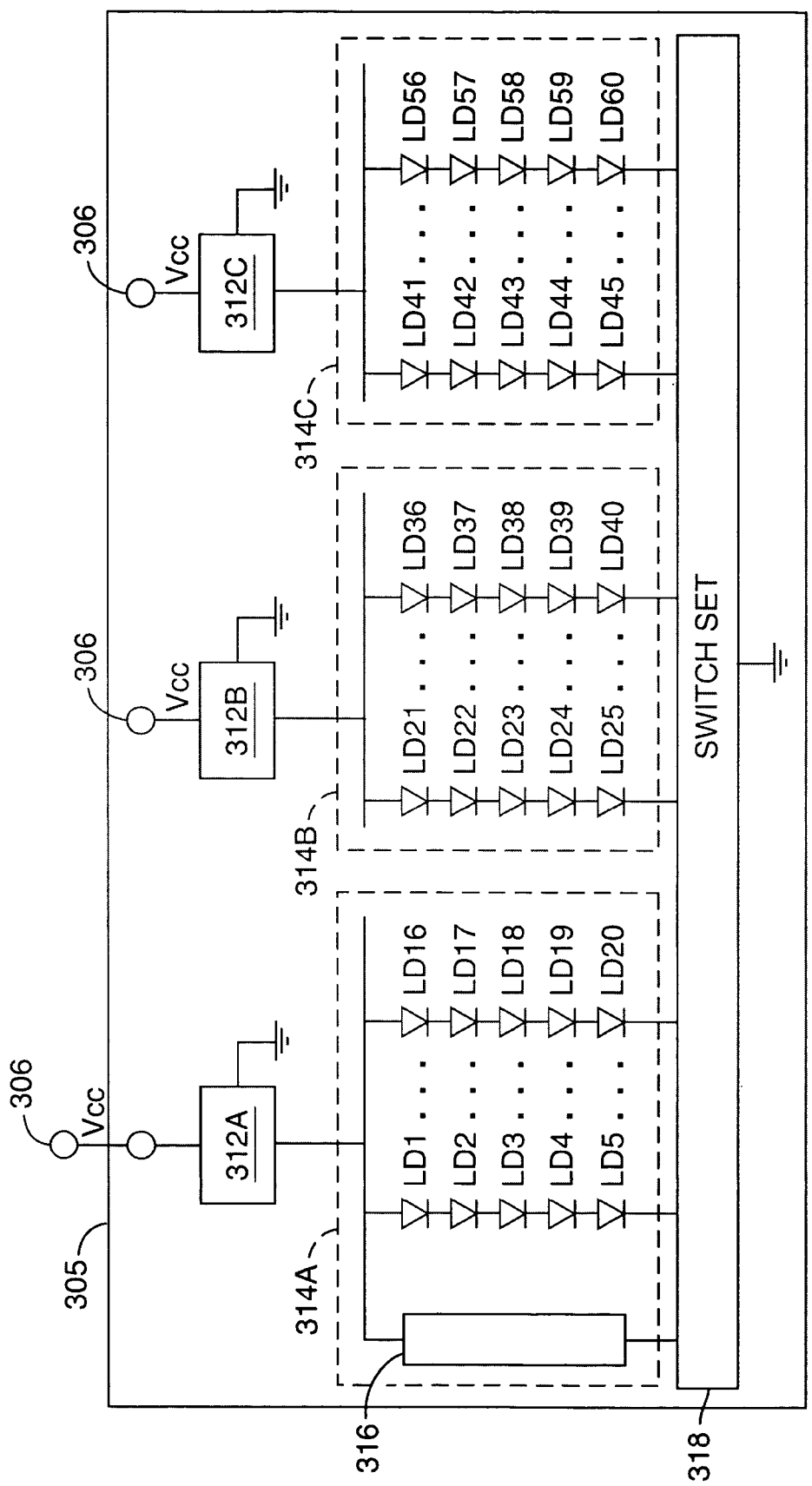
FIG. 9B shows an exemplary controller circuit adapted for pixilation in accordance with another embodiment of the present invention.

FIG. 9B shows an example control circuit 305 that can provide pixilation to the array of LED dies contained in the solid state light device. In this example, sixty LED dies (LD1–LD60) are provided in the LED die array, which are grouped into three large groupings (314A–314C) of twenty LED dies each, which are each further divided into smaller subgroups or channels (e.g., LD1–LD5) of five LED dies each. Overall, twelve channels of five LED dies each can be separately controlled in this exemplary embodiment. In one example implementation, in an RGB output application, a first grouping of LED dies can comprise red emitting LED dies, a second grouping of LED dies can comprise blue emitting LED dies, and a third grouping of LED dies can comprise green emitting LED dies. Alternatively, in another example implementation, first, second, and third groupings of LED dies can comprise "white" emitting LED dies.

In addition, the interconnect circuit layer is also designed to provide separate interconnection for the different LED die groupings. Different types of LED die groupings, and greater or lesser numbers of LED dies, can also be utilized in accordance with the principles described herein. With this configuration, separate RGB LED die channels can be driven to provide "white" or other colored output. In addition, should a particular diode channel fail or be dimmed due to LED die deterioration, adjacent channels can be driven at higher currents so that the output illumination appears to remain unchanged. Because of the (relatively) wide LED die spacing and/or the thermal management capabilities of the interconnect layer, greater drive currents to some of the LED die channels will not adversely affect overall performance.

In more detail, a voltage is provided to circuit 305 through power supply 306. The voltage is converted into a regulated output current/voltage supply by boost converter chips 312A–312C, and their associated electronics (not shown). In this manner, voltage variations from power source 306 can be mitigated, with the current/voltage supplied to the LED dies being maintained at a regulated level. Chips 312A–312C can comprise, e.g., LM2733 chips available from National Semiconductor. In this exemplary embodiment, driving voltage/current parameters can be about 20 Volts at 80–100 mA, thus providing a total of about 1.0 to 1.2 A for the entire LED die array. The driving current/voltage is then supplied to the different LED die channels within the array. In this example, each LED die would nominally require about 20 mA bias current, with a bias threshold increasing as the current increases, approaching about 4.0 V for a typical GaN-based LED die. Of course, differing LED die efficiencies or compositions may require differing bias and driving levels.

In addition, a resistor/thermistor chain 316 can be included in circuit 305 to set the overall maximum current for each LED die channel. Further, a switch set 318, comprising a corresponding number of LED die channel electronic switches, can be provided, whereby each LED die channel is coupled/decoupled to ground (or to power, depending on the LED orientation with respect to the switch set 318) in order to activate each particular LED die channel. The switch set 318 can be automatically controlled by a microcontroller (not shown) or a remote switch, based on the illumination parameters required for a particular application. Of course, this circuit architecture permits many implementations and permutations, as would be understood by one of ordinary skill in the art given the present description. For example, the control circuit 305 can be implemented to drive all LED dies with the same current, or alternatively, a given LED die channel can be turned on/off automatically or on command. By adding a fixed or variable resistance to the switch legs of the switch set, differing currents can be applied to each channel.

Figure 10:
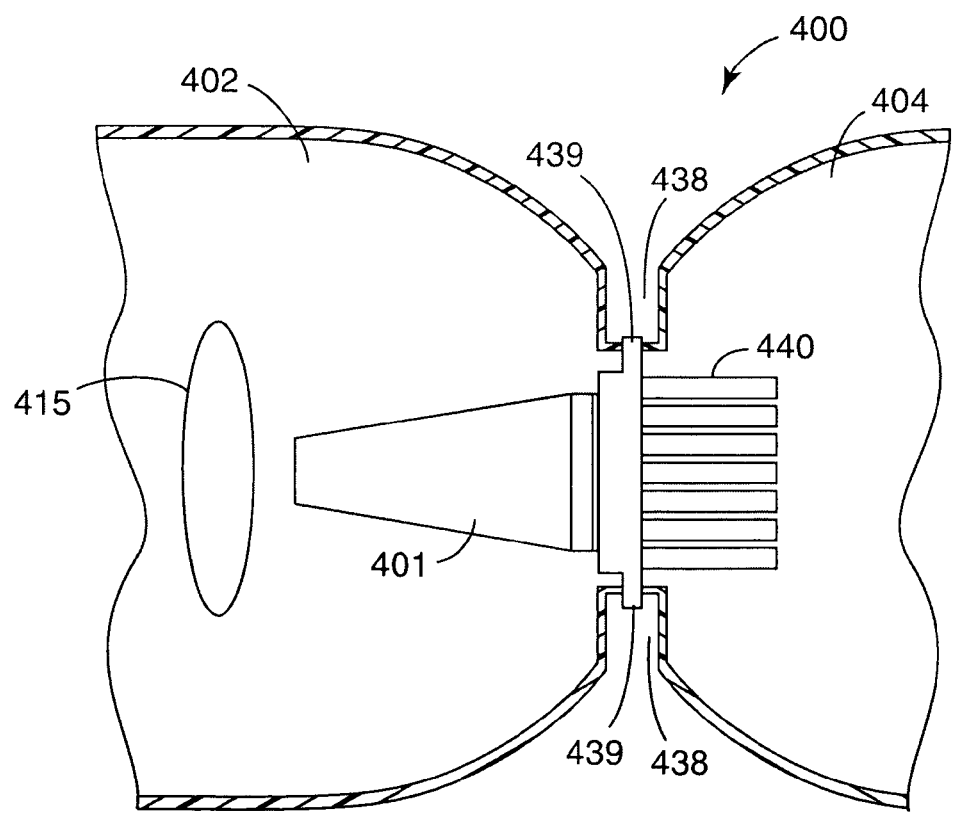
FIG. 10 shows an exemplary implementation of the solid state light device.

FIG. 10 shows a schematic illustration of an exemplary solid state light device 401 utilized in a lamp application that can be used for spot-curing. For example, solid state light device 401, which can be configured in accordance with the embodiments described above, is disposed in a compartment 402. Light device 401 can be secured in compartment 402 through the use of slidably engaging flanges 439 that are configured to slide and lock within slots 438 of a receptacle. Thus, the heat sink 440, which draws heat away from the direction of light output is located in a separate compartment 404. The beam-shaped output illumination can be collected/focused into a requirements-based illumination pattern by an optical element 415. Optical element 415 can be designed to provide a selected output pattern that complies with applicable standards. Example optical elements can include aspheric/anamorphic optical elements, and/or discontinuous and/or non-analytic (spline) optical elements.

With this approach, the use of complicated reflection optics disposed in compartment 402 can be avoided. In addition, as heat is drawn away from compartment 402, there is no need to specially heat-treat any remaining optical elements in compartment 402, thus avoiding potential performance degradation caused by exposure to continual high intensity heat. Further, if solid state light device 401 is provided with an output fiber and output aperture structure such as shown above in FIGS. 6A–6C, steerable output illumination can be accomplished without having to utilize moving mirror, bulb, and/or lens mechanisms that currently must be employed when steering the output from conventional HID lamps.

Figure 11:
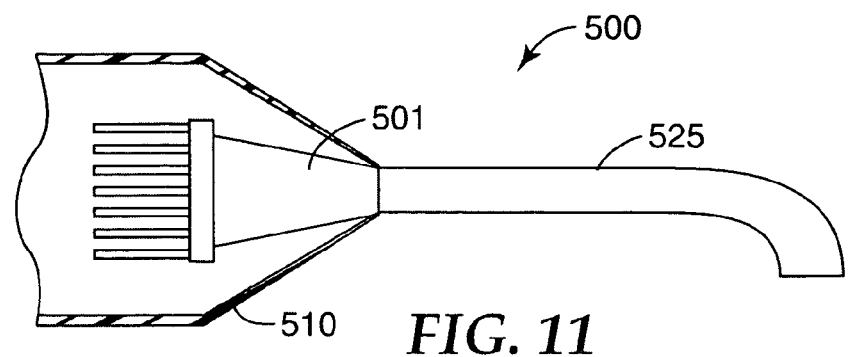
FIG. 11 shows another exemplary implementation of the solid state light device, here utilized as part of a dental curing apparatus.

The solid state light device described herein may also be utilized in other applications. For example, FIG. 11 shows a schematic highly-localized (e.g., dental) curing application, where solid state light device 501 (having a similar construction to that shown in FIGS. 1A and 1B, and/or other embodiments herein) is contained in curing apparatus 500. The solid state light device 501 can be disposed in a handle portion 510 of curing apparatus 500. In addition, the output fibers used to receive and guide the output from the LED dies or other solid state light generating sources may extend through a light delivery arm 525 that can be placed directly over the curable material. In this application, UV and/or blue radiation sources may be utilized depending on the curing aspects of the materials receiving the illumination.

Figure 12:
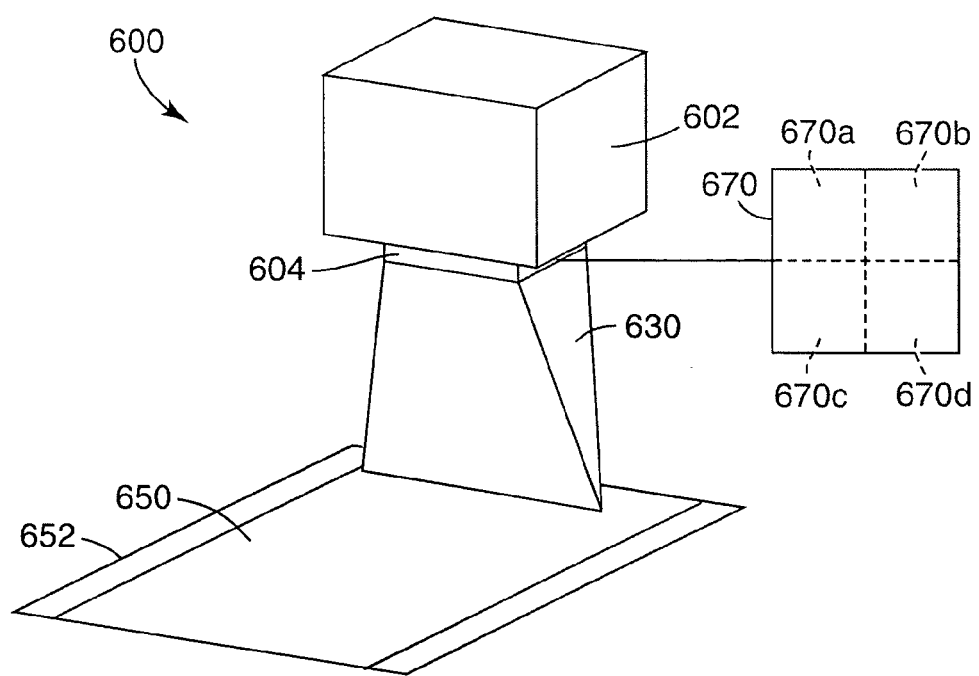
FIG. 12 shows a radiation curing apparatus according to another exemplary embodiment of the present invention.

In an exemplary embodiment shown in FIG. 12, a schematic material-curing apparatus, such as a web curing station, is provided. For example, in adhesive, tape, or web-based manufacturing, the radiation-curable agent is often a blue/UV curable material that must be cured on a different material or substrate. In conventional methods, high intensity discharge, arc lamps, and microwave-driven lamps are often utilized to perform the curing process. However, these conventional lamps radiate light and heat in 360 degrees and therefore require complicated heat exchange and/or cooling mechanisms. Alternatively, the substrate material and UV curing agent must be adapted to withstand high intensity heat in some conventional approaches.

A solution to the heating problems found in conventional curing systems is schematically illustrated in FIG. 12, where a curing station 600 comprises a solid state light device 604 (constructed similarly to those embodiments described above, such as in FIGS. 1A and 1B), where the heat dissipation or heat sink component of the solid state light device can be coupled to or replaced by a heat exchange unit 602. As discussed above, heat generated by the radiation sources of the solid state light device is drawn away from the direction of the light output by proper LED die spacing, thermally conductive interconnect circuitry, and/or heat sinks. Curing station 600 can be utilized for continuous curing operations and/or for piece parts, spot curing, or sheets.

In addition, solid state light device 604 can deliver highly concentrated radiation to radiation-curable materials, thus reducing the deleterious effects caused by poor depth of cure, which may be evident when using conventional LED arrays for radiation curing. For example, as is described above with respect to FIGS. 1A, 1B, and 2, the LED die footprint can concentrated to a fraction of the original LED die array area. For example, the footprint of the output ends can be a factor of 2–5 times smaller than the footprint of the LED die array, with a corresponding intensity increase (including coupling losses) per unit area at the end of the fiber array. For example, each LED die can be a GaN-based LED die with an output power density approaching 100 mW/cm$^2$ per die of nominal 365-nm radiation. A resulting irradiance value can approach, or even exceed, the output of a conventional high power (600 W/in), focused mercury ultraviolet lamp, which typically outputs about 2 W/cm$^2$ of nominal 365-nm radiation.

The concentrated output of the LED dies or other radiation-generating source can be collected and guided by the waveguide array, disposed in strain relief housing 630, and delivered to a radiation-curable material or formulation 650. Radiation-curable materials can include, for example, acrylate or epoxy monomers and/or oligomers, with a suitable photo-initiator or blend. The radiation-curable material or formulation 650 can be disposed on a substrate 652. Example substrates can include continuous polymer, textile, metallic foil, and the like.

The substrate 652 can be disposed on a platform, such as a moving platform or conveyor belt, or substrate 652 can be suspended between moving rollers (not shown), to provide for sheet or continual curing of large quantities of material. As mentioned above with respect to FIGS. 5A–5F, the output ends of the waveguides, e.g. optical fibers, can be arranged in a number of different reconfigurable patterns, thus making the solid state light device particularly suited for curing materials having a wide variety of shapes, and/or curing depth requirements.

For example, as mentioned above, the output ends of the fibers can be arranged in a selected pattern. In curing applications, selected patterns can be chosen to provide for curing of piece-part substrates having corners, crevices, and other structures that do not receive uniform curing radiation from conventional "flood"-type sources. In this manner, shadow effects can be reduced by proper arrangement of the output ends of the fibers.

In addition, apparatus 600 can further comprise a controller 670 that is coupled to solid state light source 604. Controller 670, which can be implemented as a single controller unit or as a set of controller units, can be adapted to selectively activate different LED dies of the LED die array to emit radiation corresponding to preferential absorption bands of exemplary photo-initiators and/or to cure different types of formulations. For example, controller 670 can include multiple different control sections (for example, control sections 670a–670d) that correspond to different LED die sections or individual (independent) channels within the LED die array of solid state source 604. Alternatively, multiple, independent controller units can be used to control each LED die channel individually. The control can be accomplished using electrical or mechanical switching, e.g., using toggle switches (not shown).

Each LED die section can comprise, for example, a set of LED dies that emit radiation at a different wavelength from the other sets of LED dies and/or irradiate a different section of the radiation curable material 650. Using the exemplary pixilation circuitry described above, apparatus 600 can thus provide greater flexibility in curing different types of materials using the same curing device. For example, one or more groups of the LED dies can be selectively activated, e.g., switched on or off, to accommodate one or more photoinitiator(s) in the curable material.

In this exemplary embodiment of the present invention, emitted radiation from a plurality of solid state sources can be concentrated into a predefined pattern such that an irradiated surface receives much higher intensity than could otherwise be attained with said sources located in close proximity to each other and said irradiated surface. The above-described curing apparatus can be utilized for continuous substrate, sheet, piece part, spot curing, and/or 3D radiation-cure processes.

As compared to conventional curing devices that use lamps, the curing apparatus 600 of FIG. 12 may provide longer lifetimes, less power requirements, greater efficiency, small form factors (for tight clearance cure applications), with little or no emitted infrared radiation to the substrate and/or chemistry (which is of particular importance for heat-sensitive product constructions).

According to this exemplary embodiment of the present invention, high irradiance levels can be attained from short wavelength (<500-nm), lower intensity LED dies through the use of optical concentrating elements coupled with optical waveguides, whose output can be selectively patterned. In this manner, shorter wavelength LED dies can be utilized without suffering from conventional low irradiance problems. In addition, a wide range of photoinitiators and photoinitiator blends can be used in the curing material 650. Example photoinitiators can include ITX and Camphor Quinone (available from Biddle-Sawyer), TPO-L (available from BASF), and IRGACURE and DAROCUR series initiators (available from Ciba Specialty Chemicals).

Also, by using the above-described optical fiber-concentrator construction, LED dies can be spaced apart at distances (e.g., at least 6 die widths or greater) that are suitable for straightforward thermal management and electrical connections. The resulting efficient heat dissipation can effectively extend the lifetimes of the LED dies and maintain higher irradiance. In addition, current/power driving requirements per LED die can be reduced without affecting irradiance levels, as more LED dies can be utilized within a relatively small footprint. Thus, longer overall die lifetime can be achieved according to exemplary embodiments of the present invention.

A problem associated with low irradiance is that if irradiance is too low, the rate of cure towards the bottom of a relatively thick radiation-curable formulation is reduced. Therefore, depth of cure and adhesion can become problems with some conventional LED-based approaches. Problems with depth of cure are intensified if the formulation contains scattering centers or radiation absorbing particles, pigments, or dyes. Moreover, further problems can arise if the radiation must pass through a carrier film or a roll before reaching the formulation.

As a solution, apparatus 600 can further include a lens or a plurality of lenses can also be formed integral with (e.g., fiber lenses) or placed separate from the ends of the fibers to further concentrate or collimate the radiation to the material or formulation being cured. Such lenses can facilitate the curing of relatively thick and/or high absorption and/or scattering formulations and for orientation of a component(s) within the irradiated formulation. For example, a lens or lens array (not shown in this figure) can be disposed at a selected distance from the output ends of the fibers/waveguides. As mentioned previously, as the heat generated from the radiation sources is drawn away from the direction of emission, the additional output collimating/focusing lenses need not be specially treated for continual heat exposure.

In addition, according to this exemplary embodiment of the present invention, apparatus 600 can provide a more uniform curing beam by extending a concentrated pattern into a cross-machine direction (CMD) and/or machine direction (MD) array. In conventional lamp-based systems, lamps have at least 15% variation across their lengths. In some cases, the uniformity variation for lamps can degrade to 30–40% over time. In conventional LED-based approaches, LEDs in an array are separated such that separation leads to irradiance non-uniformity across the array. This non-uniformity can cause potentially detrimental effects on the final product properties due to uneven cure.

The curing apparatus of the present invention can also utilize an array of LED dies of different types that can be controlled through the pixilation circuitry described above in FIGS. 9A and 9B. For example, since the output ends of the fibers can be tightly coupled, different types of LED dies (e.g., of varying intensity and/or wavelength) can be incorporated into the LED die array, thereby creating a wavelength and/or intensity-selective curing apparatus, with minimal loss in uniformity in the machine- and cross-machine directions. In addition, incorporating different wavelengths of LED dies into the LED die array may be utilized to emit radiation at selected wavelengths coinciding to preferential absorption bands of exemplary photo-initiators such as, e.g., a blend of ITX and TPO-L.

Thus, curing apparatus 600 can be designed to cure with different wavelengths and/or intensities so that the same curing apparatus can be used to cure different types of formulations, making apparatus 600 suitable for laboratory, pilot, and production lines that process different formulations that require different radiation wavelengths and intensities. In addition, with the pixilation controller circuitry described herein, apparatus 600 can be controlled to selectively activate particular LED dies or LED die groupings depending on the type of material being cured. In contrast, with conventional approaches, a LED array is usually configured with only one particular type of LED. Thus, when a different wavelength or intensity is needed with a conventional system, a new array is required to accommodate the formulation absorption. This leads to additional modules that require more equipment costs and more potential maintenance.

Apparatus 600 is also suitable for high resolution curing of patterns, 3-dimensional structures, lithography, and masking. For example, as the output ends of the fibers can be secured in a reconfigurable banding, such as banding 156 from FIG. 11B, the output ends of the fibers can be arranged into a pattern to cure a particular 3-dimensional structure and/or part. In addition, for substrate-based processes, apparatus 600 can provide high-resolution irradiance profile curing in the cross-machine and machine directions. As the output ends of the fibers may be tightly bundled or tightly patterned, the LED dies may be driven at varying intensities to create a smooth intensity profile, with resolution being on the order of the fiber diameter. In contrast, conventional LED arrays that are spaced further apart (for thermal purposes) provide a variable intensity profile.

Figure 14:
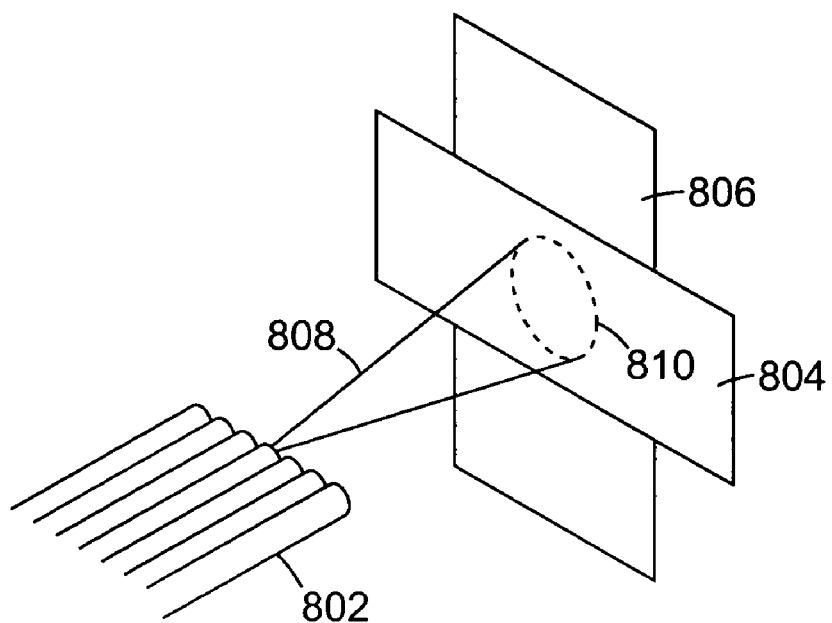
FIG. 14 shows a radiation modifying apparatus that includes a polarizer and that is treating a radiation modifiable material disposed on a substrate.

Now turning to FIG. 14, an example of a modifying apparatus configuration is shown whereby light emitted from a waveguide 802 is polarized prior to striking a radiation polarizable material. As shown in FIG. 14 as well as FIGS. 15–18 discussed below, the waveguide 802 is linear, but it will be appreciated that two-dimensional arrays are also applicable. The waveguide 802 outputs light 808 that is not polarized such that the waves of electromagnetic energy are randomly aligned. However, for some modifying applications, it is preferred to treat the radiation modifiable material with polarized light. One example of such a modifying application is the treatment of liquid crystal material. Another example is the treatment of polymer chains. In these cases, it is desired that the liquid crystals or polymer chain bonds become aligned a certain way. The liquid crystals or polymer bonds align themselves according to the alignment of waves of electromagnetic energy of the radiation that strikes the subject material. Therefore, polarizing the light prior to it striking the subject material results in liquid crystals or polymer bonds aligning themselves with the aligned waves.

In the example of FIG. 14, the light 808 emitted from the waveguide 802 emanates directly to a polarizer 804 where it covers an essentially circular area 812. As the light 808 that is emitted directly from the waveguide 802 has a relatively broad angle of emission, the polarizer 804 must have a broad acceptance cone to avoid wasting light that has been emitted from the waveguide 802. Even with an efficient polarizer for the particular wavelength of radiation, the polarized light passing through the polarizer 804 and striking the substrate 806 upon which the radiation modifiable material is disposed has a relatively low intensity.

Various polarizer designs are applicable. For infra-red and visible light wavelengths, acceptable polarizers include but are not limited to Brewster stacks, coated plates, multi-layer optical films, absorbing polarizers, and prisms. However, for UV wavelengths, acceptable polarizers typically have a narrow acceptance cone which requires that the divergence angle of the light from a wave guide be narrowed, as discussed below. Examples of a polarizer suitable for the UV application include Brewster stacks, multi-layer coated optics, wire-grids, and some prisms.

Figure 15:
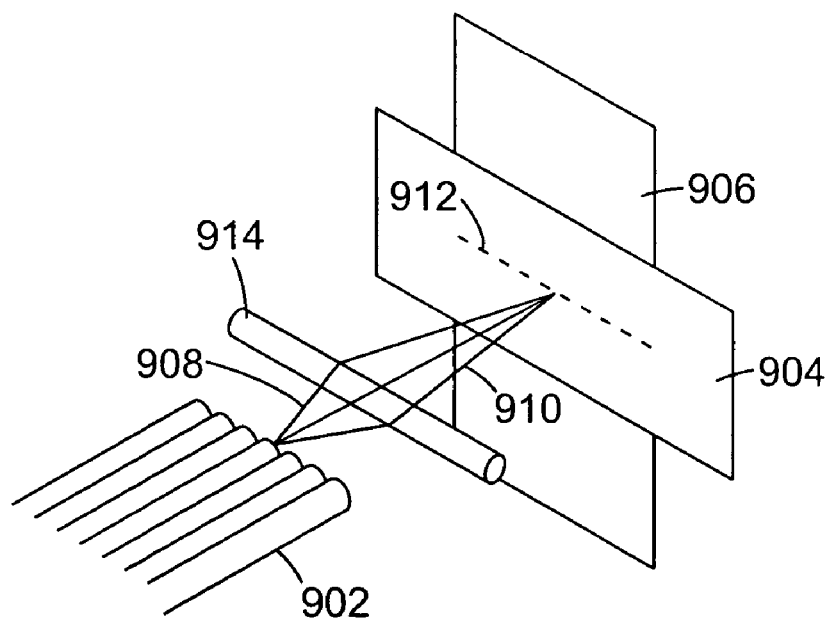
FIG. 15 shows a radiation modifying apparatus that includes both a cylindrical lens and a polarizer and that is treating a radiation modifiable material disposed on a substrate.

FIG. 15 shows an example of a modifying apparatus configuration whereby light emitted from a waveguide 902 is first focused into a line prior to being polarized. In this example, the light 908 emitted from the waveguide 902 is focused into a line along an axis of a cylindrical lens 914 placed in the path of the radiation and between the waveguide 902 and a polarizer 906. The light reaching the polarizer 906 forms a line 912 that has a higher intensity than a full cone of emitted light. Therefore, the polarized light reaching the substrate 906 upon which the radiation modifiable material is disposed will have a higher intensity.

While the cylindrical lens has focused the light from each of the fiber ends of the waveguide 902 into a line, the light 910 emanating from the cylindrical lens 914 continues to have a broad divergence angle along the axis of the cylindrical lens 914. Therefore, the polarizer 904 must also have a broad acceptance cone, at least along that same axis, to avoid wasting the light emitted from the waveguide 902. As noted above, for UV applications, acceptable polarizers have a smaller acceptance cone which requires that the divergence angle of the light be reduced, as discussed below.

Figure 16A:
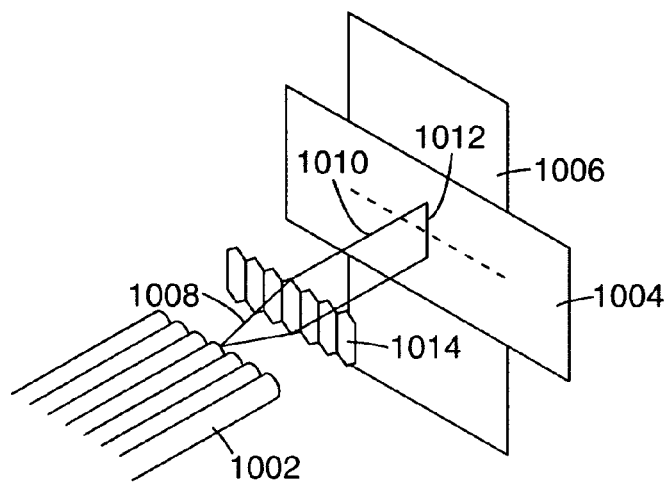
FIG. 16A shows a radiation modifying apparatus that includes both a lenslet array and a polarizer and that is treating a radiation modifiable material disposed on a substrate.

FIG. 16A shows an example of a modifying apparatus configuration whereby light emitted from a waveguide 1002 is first collimated prior to being polarized. One benefit of collimating the light is that UV polarizers may be used. In this example, the light 1008 emitted from the waveguide 1002 is collimated by a lenslet array 1014, which has a number of lenslets matched to the number and divergence angle not clear what you mean by 'cone of fibers' of fibers of the waveguide 1002. The required acceptance cone of a polarizer 1004 is determined as a function of the focal length of each lenslet of the array 1014 and the size of each fiber of the waveguide 1002, as opposed to being determined by the fiber characteristics alone. Accordingly, the lenslet array 1014 collimates the light such that the acceptance cone required for the polarizer 1004 is decreased to an amount acceptable for many polarizers, including those acceptable for UV light.

The collimated light 1010 then reaches the polarizer with the collimated light 1010 from each lenslet striking the polarizer and covering an area 1012 shaped according to the shape defined by each lenslet. As noted below with reference to FIG. 18, a cylindrical lens could be included between the polarizer 1004 and substrate 1006 upon which the radiation modifiable material is disposed to focus the light into a line of greater intensity.

Figure 16B:
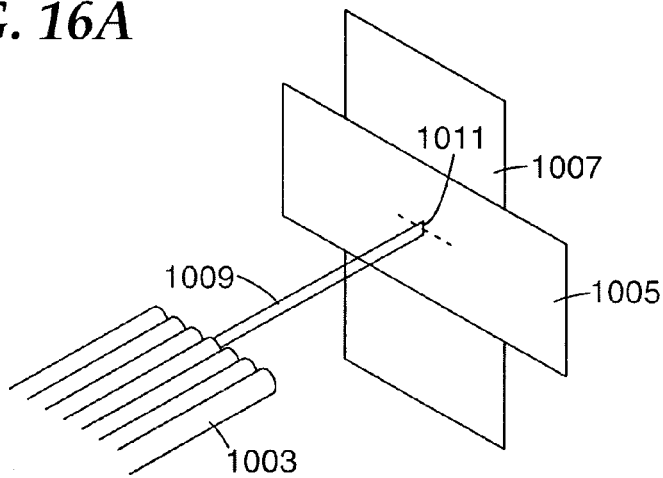
FIG. 16B shows a radiation modifying apparatus that includes both a lens formed in each fiber at an output end of a waveguide and a polarizer and that is treating a radiation modifiable material disposed on a substrate.

FIG. 16B shows a configuration like that of FIG. 16A except that a lens is formed in the end of each fiber of the waveguide 1003 such that a lenslet array is unnecessary. The lens of each fiber collimates the light from the fiber so that the collimated light 1009 has a decreased cone when striking the polarizer 1005, to cover an area 1011 shaped as defined by the lens of each fiber. Again, a cylindrical lens may be positioned on either side of the polarizer 1005 to focus the light into a line of greater intensity prior to the polarized light striking the substrate 1007 upon which the radiation modifiable material is disposed.

Figure 17:
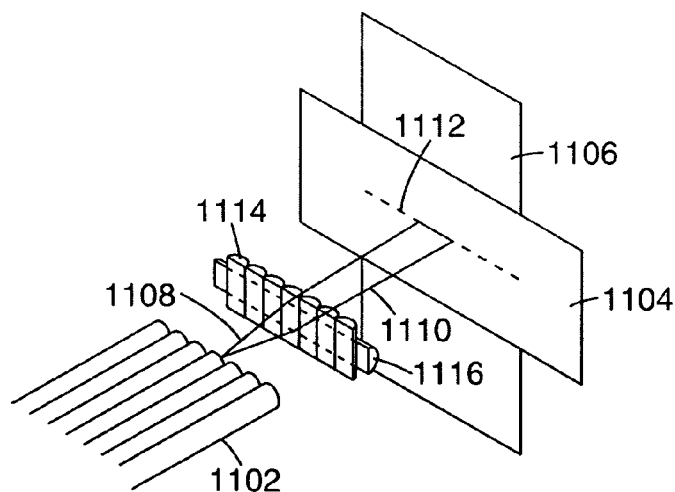
FIG. 17 shows a radiation modifying apparatus that includes a lenticular array in combination with a cylindrical lens and polarizer and that is treating a radiation modifiable material disposed on a substrate.

FIG. 17 shows an example of a modifying apparatus configuration whereby light emitted from a waveguide 1102 is first collimated and then focused into a line prior to being polarized. In this example, the light 1108 is collimated by a lenticular array 1114 in combination with a cylindrical lens 1116. It will be appreciated that the lenticular array 114 has a lens for each fiber, and the size of the fiber and focal length of the lenses determines the required acceptance cone for the polarizer 1104. Again, the lenticular array 1114 collimates the light such that the acceptance cone required for the polarizer 1104 is decreased to an amount applicable for many polarizers, including those acceptable for UV light.

The collimated light 1110 strikes the polarizer 1104 and covers a relatively focused linear area 1112. The polarized light then strikes the substrate 1106 upon which the radiation modifiable material is disposed. As noted below with reference to FIG. 18, a cylindrical lens may be included between the polarizer 1104 and the substrate 1106 to further focus the light into a line of greater intensity. Furthermore, in embodiments where the lenticular array 1114 is made of a flexible material, the lenticular array 1114 may be bent into a bowed shape to perform the focusing function of the cylindrical lens 1116.

Figure 18:
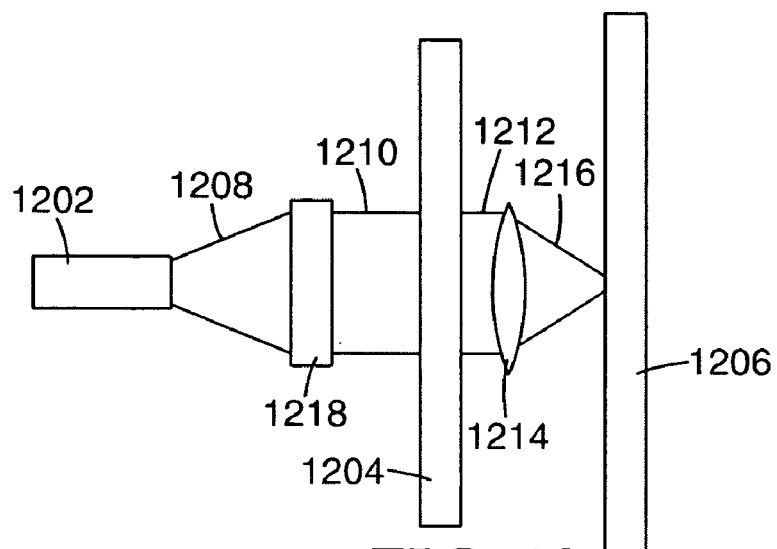
FIG. 18 shows an example of a radiation modifying apparatus that includes an optical element in conjunction with a polarizer followed by another optical element as an alternative manner of treating a radiation modifiable material disposed on a substrate.

FIG. 18 shows an alternative configuration to that of FIGS. 16 and 17. In this configuration, the waveguide 1202 emanates light 1208 that reaches an optical element 1218 such as a lenslet array of FIG. 16 or a lenticular array of FIG. 17. The optical element 1218 collimates that light, and collimated light 1210 then reaches a polarizer 1204. Again, because the light 1210 has been collimated, the acceptance cone required for the polarizer 1204 is decreased, allowing polarizers including those acceptable for UV light to be chosen. Polarized light 1212 emanating from the polarizer 1204 then strikes a second optical element 1214, such as a cylindrical lens. In the case of a cylindrical lens, the polarized light 1216 is focused into a line that then strikes the substrate 1206 upon which the radiation modifiable material is disposed.

In relation to these configurations, the parameters for the lens and polarizer as a combination may be chosen to optimize uniformity of intensity or polarization and minimize loss of light. The parameters to consider for the lens include distance of the lens from the end of the waveguide and the diameter of the lens. These parameters may be chosen in relation to known values including the fiber core diameter ($D_{fiber}$) of each fiber of the waveguide, the numerical aperture ($NA_{fiber}$) of each fiber, and the acceptance cone of the chosen polarizer.

As an example, for a chosen waveguide the fiber core diameter, $D_{fiber}$, may equal 600 μm while the numerical aperture, $NA_{fiber}$, equals 0.39. The chosen polarizer may have a full acceptance cone of five degrees in order to achieve the desired polarization state. To optimize the lens, the $D_{fiber}$ or 600 μm is divided by twice the tangent of one half of the desired divergence angle (one half of 5 degrees or less), which is 0.086 or less. This gives the minimum allowable focal length for the lens which, when positioned one focal length from the waveguide, yields light with a cone angle matching that of the acceptance cone of the polarizer. In this example, this minimum distance is 6.97 mm. Next, the minimum diameter of the lens needed to subtend the light leaving the waveguide is approximated by multiplying twice the $NA_{fiber}$ or 0.78 by the distance that has been computed, or 6.97 mm. The resulting diameter for this example is 5.44 mm. To provide some tolerance over these minimum parameters, distance to the lens may be chosen as 7 mm while the diameter of the lens is chosen as 5.5 mm. Choosing a longer focal length lens would result in less divergence, but the F-number of the lens should remain less than the inverse of twice the $NA_{fiber}$, or 1.28 in this case, in order to subtend all the light from the waveguide.

Figure 19:
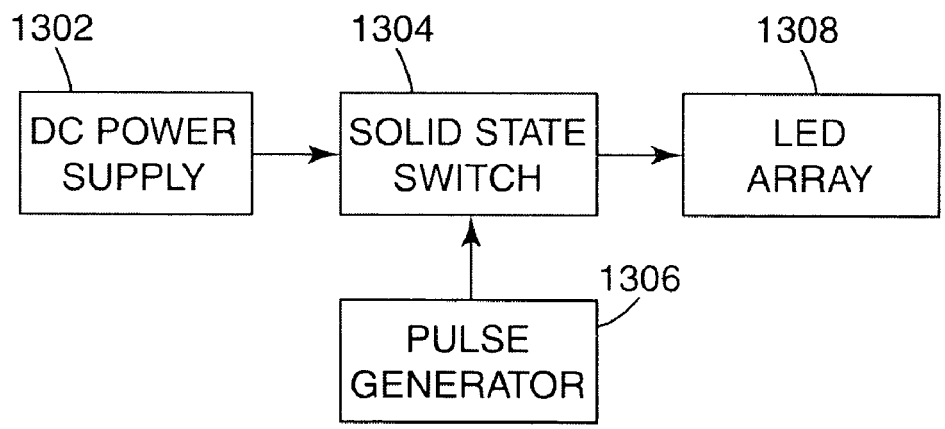
FIG. 19 shows a diagrammatic representation of a first example of a pulse control system including a pulse generator for causing an array of LEDs to generate pulsed radiation for modifying a radiation curable material.
Figure 20:
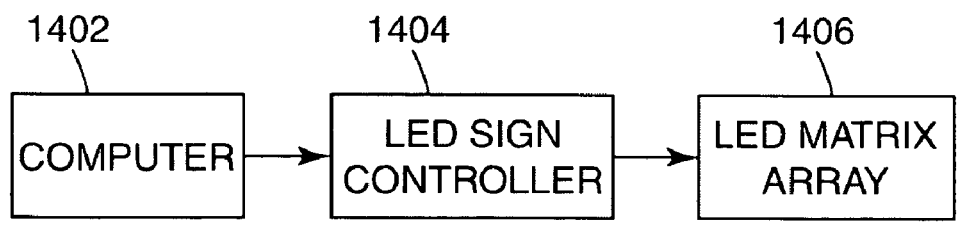
FIG. 20 shows a diagrammatic representation of a second example of a pulse control system including an LED sign controller for causing an array of LEDs to generate pulsed radiation for modifying a radiation curable material.
Figure 21:
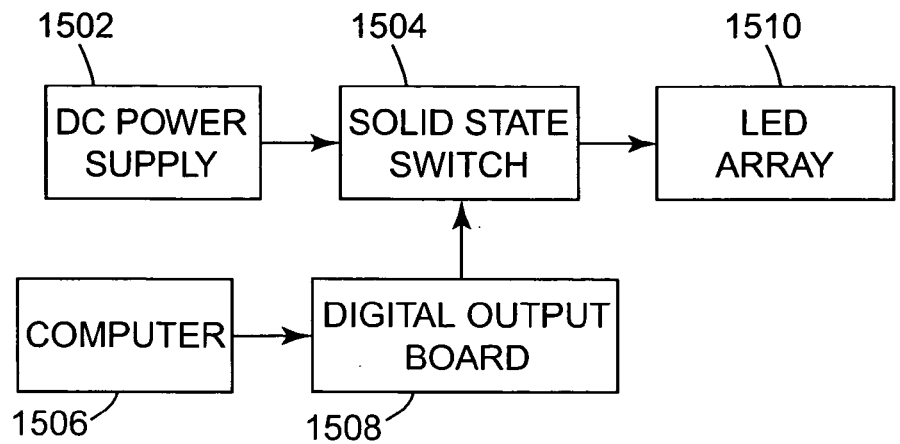
FIG. 21 shows a diagrammatic representation of a third example of a pulse control system including a computer driven output for causing an array of LEDs to generate pulsed radiation for modifying a radiation curable material.

FIGS. 19–21 shows controller configurations that allow for pulsing of the LED dies of an apparatus such as any of those described above, including those with or without lenses and/or polarizers. As discussed above in relation to FIG. 9B and as discussed in more detail below, the controller may control individual dies such that each individual die may be pulsed separately from others and may be pulsed with an intensity that differs from others. Individually controlling the activation and intensity of the LED dies of an array is discussed in more detail below with reference to FIGS. 22–25.

Pulsing of the LEDs of a curing apparatus has many advantages when compared to the application of steady-state LED radiation. A higher instantaneous irradiance can be achieved by pulsing the LEDs, which allows for curing of acrylates in air and provides for curing of thicker coatings. Furthermore, pulsing the LEDs generates less overall heat in the coating while increasing the localized peak temperature in the coating. To achieve higher irradiance, the electrical current is increased for the duration of the pulse. To prevent damage to the LED, it is turned off and allowed to cool between pulses. Advantages to pulsed LED curing include: increased depth of cure, increased rates of reaction, added oxygen depletion, and increased diffusion of free radicals to start polymerization reactions. There are also advantages to a dark cure, where the material being cured is not subjected to light during the time between pulses such that radical-radical annihilation is minimized. Specifically, where the LED dies emit UV radiation, pulsing the LEDs brings about these advantages which culminate in the production of higher molecular weight products.

The controller configuration of FIG. 19 is a configuration that provides for high frequency, short duration pulsing, which is useful for various modifications including curing acrylates in air and curing relatively thick coatings. This configuration includes a variable voltage DC power supply 1302 that provides power to a solid-state switching element 1304. For individual pulsing of LED dies, the solid-state switching element 1304 may provide individual switching for each LED die of the LED array 1308. The solid-state switch 1304 is driven by a pulse generator 1306. The pulse generator may be chosen so that it has both a variable pulsing frequency and a variable pulse width.

The output voltage of the DC power supply 1302 may be adjustable so as to provide the desired amount of drive current to the LED array through the solid-state switch 1304. An example of a solid-state switch 1304 is a power transistor, e.g. a field effect transistor (power FET), with a driver circuit that receives input from the pulse generator 1306. The pulse generator may be one of various commercially available devices, such as the model 81101A from Agilent Technologies. This particular pulse generator has a frequency ranging from 1 mHz to 50 MHz and has a pulse width as low as 10 ns. It is known that the optical rise time of a UV LED, such as those offered by Cree Optoelectronics, is on the order of 30 ns.

The controller configuration of FIG. 20 provides for low frequency and long duration pulsing. This configuration includes a personal computer 1402 that is used to program a commercially available LED sign controller 1404 to provide pulsing. The LED sign controller 1404 then pulses each of the LEDs of an LED matrix array 1406 as if the LED matrix array 1406 is an LED sign that is blinking. Because the LED sign controller 1404 is designed to control a visible sign, the pulse frequency is much lower and on the order of 25 Hz.

FIG. 21 shows yet another controller configuration that provides for a medium frequency and duration of pulsing. This configuration includes a variable voltage DC power supply 1502 that provides power to a solid-state switching element or switching array 1504. The solid-state switch array 1504 is driven by a digital output board 1508 configured as an X and Y array that is in turn controlled by a personal computer 1506. The personal computer 1506 may implement a control program such as a National Instruments LabVIEW Virtual Instrument program to control a National Instruments digital output board 1508. The program allows for the LEDs to be pulsed at random or at a specific frequency, typically in the kilohertz range.

Figure 22:
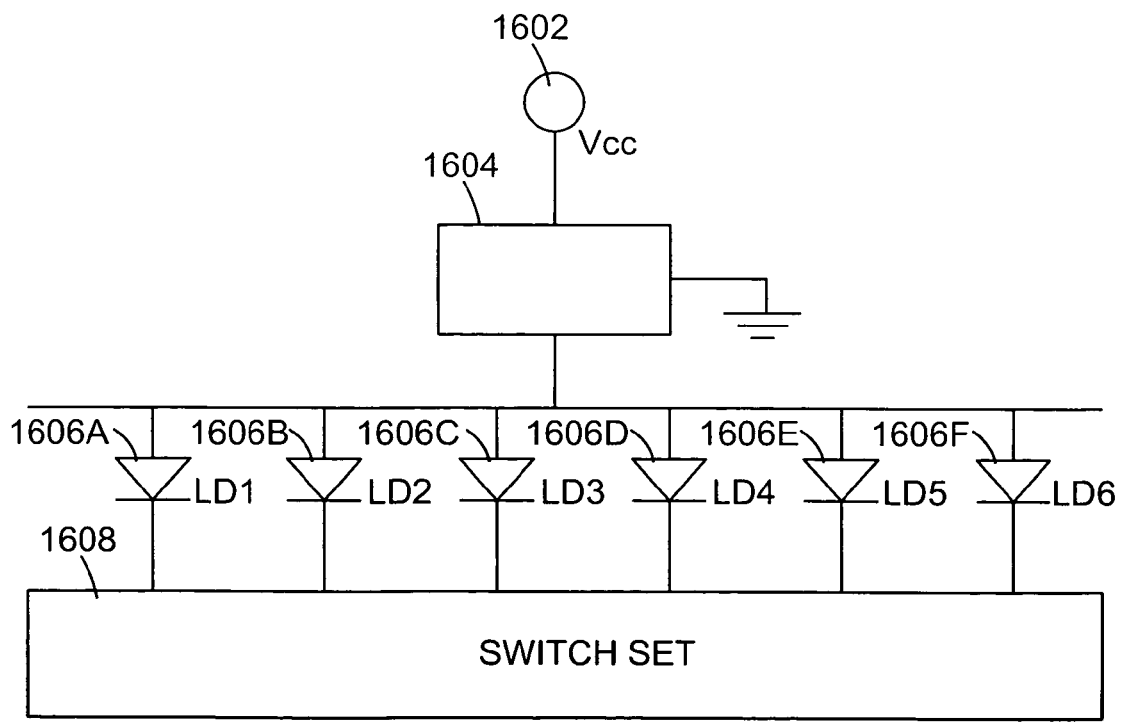
FIG. 22 shows another adapter circuit for increased resolution of an LED array relative to the adapter circuit of FIG. 9.

FIG. 22 shows an example of a circuit where an individual LED die forms its own channel so that curing or other modification can be done at a high resolution, as previously discussed above in relation to FIG. 12. Each LED can be selectively and individually activated in relation to other LED dies of an array. Accordingly, patterns can be created in radiation modifiable material by activating only the LEDs necessary to create the pattern, as opposed to all LEDs of an array. FIG. 22 includes a Vcc power source 1602 that provides power to a booster circuit 1604, such as that discussed above with reference to FIG. 9B. The booster circuit 1604 then provides power to individual channels 1606A–1606F, where each channel is a single LED die. A switch array set 1608 then selectively activates one or more of the channels, which in turn selectively activates one or more individual LED dies. Accordingly, the switch array set 1608 may be configured to activate only those channels necessary to create the desired pattern.

This circuit may be used in conjunction with any of the techniques noted above. For example, this circuit may be used in conjunction with or without lenses and/or polarizers. Furthermore, this circuit may be used with or without a pulsing controller. When a pulsing controller is included, the switch set 1608 allows current to pass through the selected LED dies in accordance with the provided pulsing signal.

Figure 23:
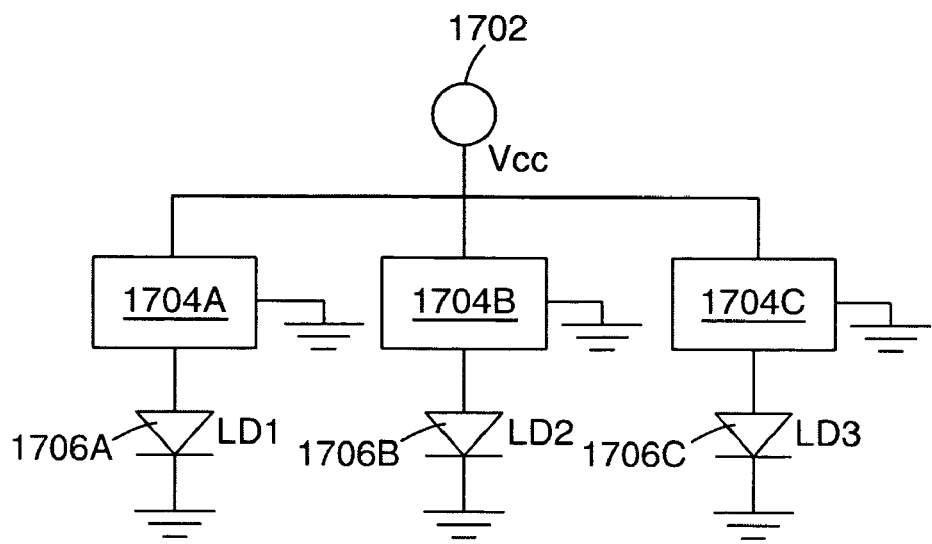
FIG. 23 shows another adapter circuit for increased intensity control for an LED array.

FIG. 23 shows an example of a circuit where an individual LED die 1706A–1706C forms its own channel so that curing can be done at a high resolution, and each channel has its power control circuit 1704A–1704C connected to a Vcc power source 1702 so that the intensity can be controlled for each individual LED die. Individually controlling the intensity of each LED die 1706A–1706C through each individual booster circuit 1704A–1704C allows for profile curing or other profile modification to be performed, whereby the irradiance provided across the waveguide is not uniform in order to match a target that is also not uniform.

This circuit may also be used in conjunction with any of the techniques noted above. For example, this circuit may be used in conjunction with or without lenses and/or polarizers and with or without a pulsing controller.

Figure 24:
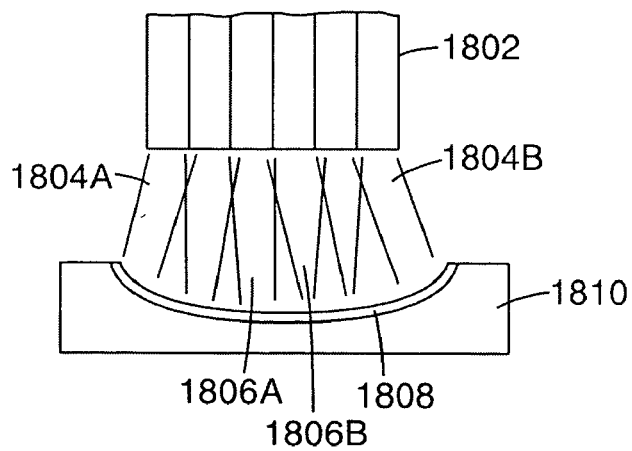
FIG. 24 shows uniform radiation modification of a radiation modifiable material located upon a non-uniform structure in accordance with the adapter circuit of FIG. 23.

FIG. 24 shows an example of a target that is not uniform. In this example, the target is a curable material 1808 positioned on a non-uniform structure 1810. Specifically, the structure 1810 of this example is U-shaped such that the radiation curable material is farther from the waveguide in the center than at the ends. Accordingly, if uniform irradiance was provided across the waveguide 1802, then the surface of the material 1808 would not receive relatively uniform irradiance. Instead, the ends would receive irradiance of a greater intensity than the irradiance at the center.

To counter the U-shaped structure 1810, the waveguide 1802 outputs an irradiance that is not uniform at the waveguide 1802. The intensity of the irradiance beams 1804A and 1804B on the ends is lower at the waveguide than the irradiance of beams 1806A and 1806B in the center. Accordingly, the irradiance reaching the material 1808, as well as the resulting curing, is more uniform from side to side.

Figure 25:
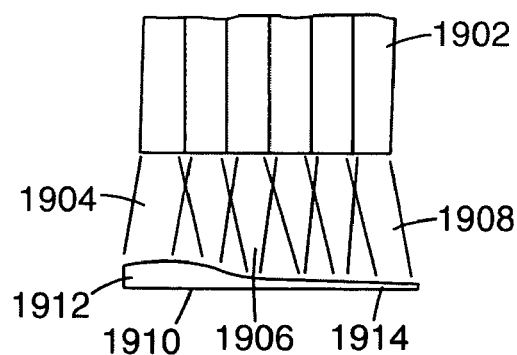
FIG. 25 shows uniform radiation modification of a radiation modifiable material having varying thickness disposed on a substrate.

FIG. 25 shows another example of a target that is also not uniform. However, in this example, the target is curable material 1910 that has a varying transmissibility, specifically thickness, from one end to the other. Therefore, if the irradiance at the waveguide 1902 was uniform, then the irradiance at the surface of the material would be less effective at the thick end 1912 relative to the thin end 1914 such that curing throughout the coating may not be relatively uniform.

To counter the variance is transmissibility of the material 1910, the waveguide 1902 outputs an irradiance that is not uniform at the waveguide 1902. The intensity of the irradiance beam 1904 which is aimed toward the thick end 1912 is highest. The intensity of the irradiance beam 1906 which is aimed toward the middle of the material has a lower intensity than beam 1904 but has a higher intensity than the irradiance of beam 1908 which is aimed toward the thin end 1914. Therefore, the curing of the material 1910 is more uniform from side to side.

Figure 26:
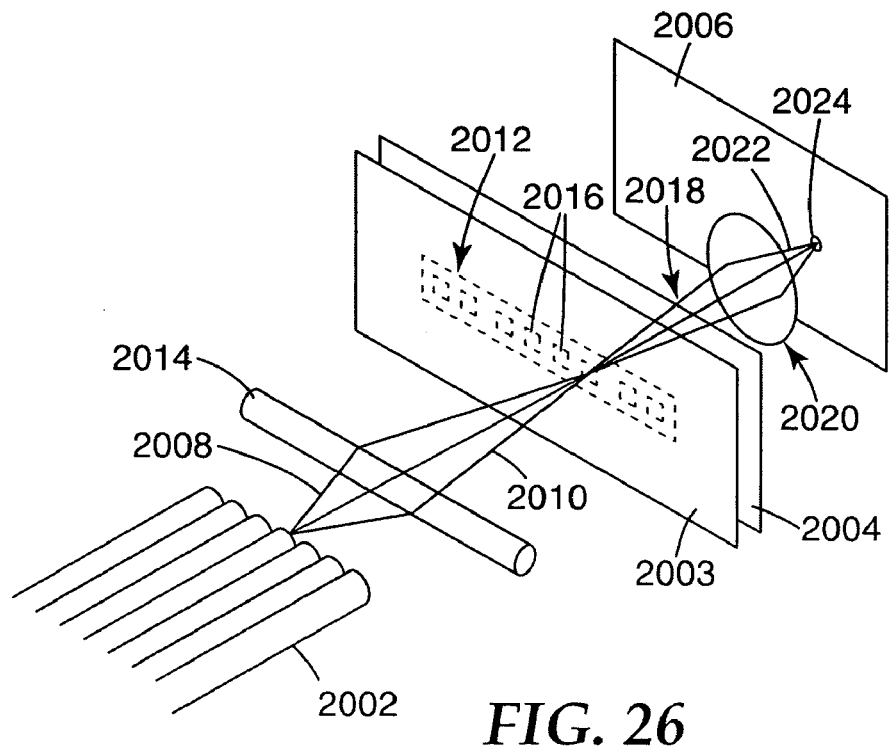
FIG. 26 shows a radiation modifying apparatus that utilizes a light valve to provide high-resolution modification.

FIG. 26 shows an alternative manner of controlling the application of radiation from a waveguide 2002 to a radiation modifiable material 2006. The radiation from the individual fibers of the waveguide 2002 can be controlled by a light valve structure 2012 placed in the pathway of radiation emanating from the waveguide 2002. The light valve structure 2012 operates to control the passage of light to the modifiable material. As shown, the light valve 2012 may operate in conjunction with a set of polarizers 2003, 2004 to allow for the radiation from a given fiber to be blocked, to allow for substantially all radiation from a given fiber to pass through, or to apply a continuously variable reduction in intensity of radiation from a given fiber. Furthermore, the light valve may be configured in a static or mask condition or the light valve may be controllable such that it is dynamic.

As shown, the light valve structure 2012 is a one dimensional array of light valve cells 2016 where each of the light valve cells 2016 are individually controllable to thereby dynamically control the passage of received radiation. As used herein, the term light valve refers generally to either to a light valve structure 2012 that includes a plurality of light valve cells 2016 or to an individual light valve cell 2016. It will be appreciated that a complete light valve structure 2012 or only an individual light valve cell 2016 may be placed in the pathway of radiation.

There are various forms of light valves that may be used. As shown in FIG. 26, a liquid crystal display ("LCD") array may be provided. The LCD array uses LCD cells as the individual light valve cells 2016. A standard LCD controller (not shown) selectively controls the individual LCD cells to cause them to control the rotation of polarization of light that passes through. Other examples of light valves include grated light valves and digital mirror devices. Grated light valves use light valve cells that include multiple electrostatically controlled reflective ribbons that form a diffraction grating. The grated light valve example employs an alignment of the light valves relative to the waveguide 2002 and material 2006 to account for the reflection provided by the individual light valve cells, as opposed to a straight line approach as shown for the LCD light valve. Examples of configurations utilizing grated light valves or digital mirror devices that rely upon deflection to control the intensity of light are discussed in more detail below with reference to FIG. 28.

The LCD light valve of FIG. 26 controls the intensity of light that reaches the modifiable material by working in conjunction with an initial polarizer 2003 and a final polarizer 2004. The initial polarizer 2003 gives the light a particular polarization. The LCD light valve 2012 then rotates the polarizer by a given amount, anywhere from zero to 180 degrees. The radiation must then pass through the final polarizer 2004. However, only light with a proper polarization state passes through the final polarizer 2004 with normal intensity. If the polarization state is 90 degrees from the required polarization state for the final polarizer 2004, then no radiation passes through. Accordingly, the LCD light valve 2012 can be utilized to rotate the polarization state as desired to thereby control the amount of radiation that will pass through the final polarizer 2004. Because the individual LCD cells 2016 can be independently controlled, the radiation passing through some LCD cells may be given a different polarization rotation than radiation passing through other LCD cells such that a pattern of radiation emanates from the final polarizer 2004.

As light valves control the intensity of radiation reaching the radiation modifiable material, light valves may be used to either create patterns in the material or to improve the uniformity of the curing or other modification for a highly non-uniform material or material position such as shown in FIGS. 24 and 25. The intensity of light that passes through the light valve is controlled to produce the desired pattern or alteration to the intensity profile across the light valve. Accordingly, the intensity from the individual fibers may be substantially uniform, as opposed to controlling the activation and/or intensity from each as described above in relation to FIGS. 22–25.

As discussed, this example of FIG. 26 shows a one dimensional array of light valve cells 2016. It will be also appreciated that other array dimensions are also applicable. However, as shown in this example it may be desirable when applying arrays, such as a one dimensional array 2012, to focus the light emanating from the waveguide 2002 onto the array 2012 by using an optical element. The light is focused so that substantially all of the light from the waveguide 2002 must pass through the light valve structure 2012 prior to reaching the material 2006. In the example shown, a cylindrical lens 2014 is placed in the path of radiation 2008 emanating from the waveguide 2002 so that light 2010 emanating from the cylindrical lens 2014 becomes focused on the light valve 2012.

Furthermore, it may also be beneficial to further alter the passage of radiation emanating from the second polarizer 2004. In the example shown, a second optical element 2020 is included between the polarizer 2004 and the modifiable material 2006. Specifically, this second optical element of this example is a projection lens which takes the light diverging from the polarizer and again focuses it toward a point 2024 on the modifiable material 2006. The collection of points 2024 forms a line that follows the pattern or intensity profile as dictated by the light valve 2012.

Another enhancement that may be used in conjunction with the light valve that has multiple dimensions includes an angle control element such as a prismatic film (not shown). The prismatic film is placed between the waveguide 2002 and the light valve 2012 to better utilize high angle light leaving the waveguide 2002.

Figure 27:
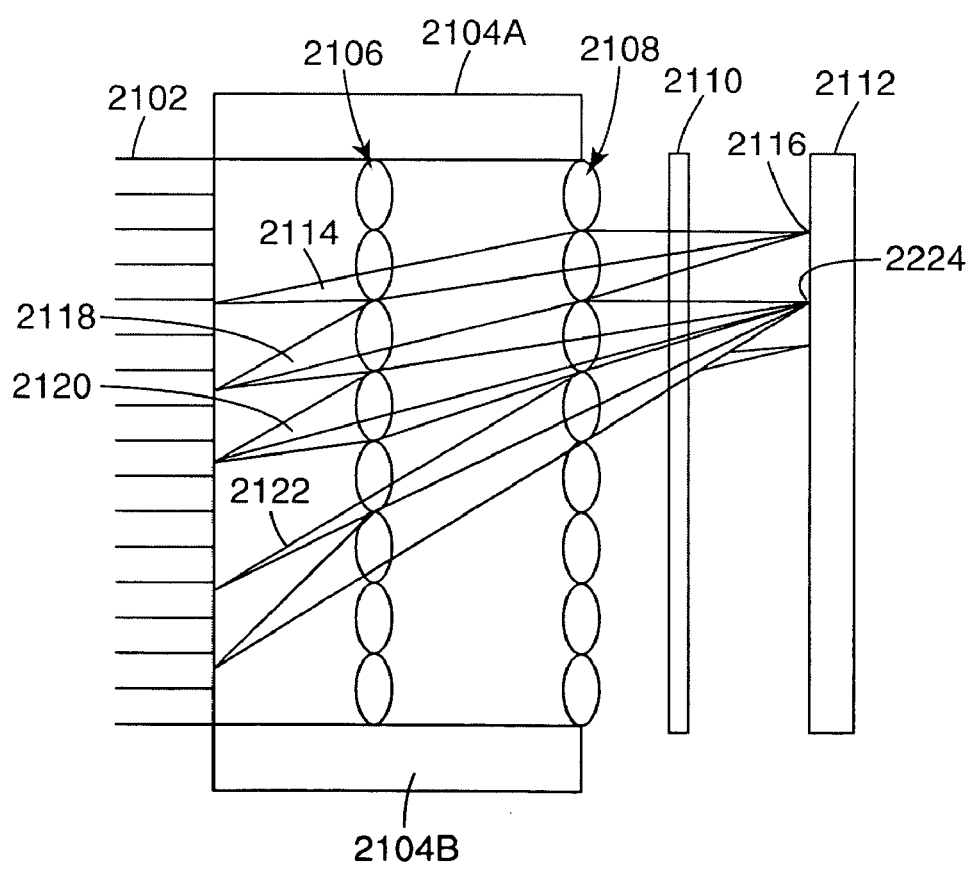
FIG. 27 shows a radiation modifying apparatus that utilizes one or more optical elements to smooth an intensity profile applied to a radiation modifiable material.

FIG. 27 shows a radiation modifying configuration that utilizes optics to smooth the intensity profile being applied to the radiation modifiable material. A waveguide 2102 outputs radiation toward an optical element 2106, such as a lenslet array. To provide the effect of an infinite waveguide 2102, mirrors 2104A and 2104B may be included to reflect errant radiation back toward the optical element 2106. In this example, an optional second optical element 2108 such as a lenslet array is also included to further collimate light emanating from the first optical element 2106. An optional blur filter 2110 is disposed between the second optical element 2108 and the radiation modifiable material 2112.

Several angles of radiation pathways as well as angles of non-radiation pathways are illustrated in FIG. 27 to demonstrate the smoothing effect. Non-radiation pathway 2114 extends from the small area between fibers of the waveguide 2102 from which no radiation emanates. As shown, this pathway 2114 extends to a point 2116 on the modifiable material 2112. However, rather than this point 2116 being exposed to no radiation, radiation pathway 2118 extends from a central region of a fiber to point 2116 such that the otherwise unexposed point 2116 receives radiation. Similarly, point 2224 receives no radiation via a high angle pathway 2122. However, point 2224 receives radiation via pathways including pathway 2120. Accordingly, the optical elements 2106 and optionally 2108 create a non-imaging configuration whereby the light emanating from the waveguide 2102 is blurred at the material 2112 rather than being directly imaged. The blur filter 2110 may be included to further blur the radiation to smooth the intensity profile.

Figure 28:
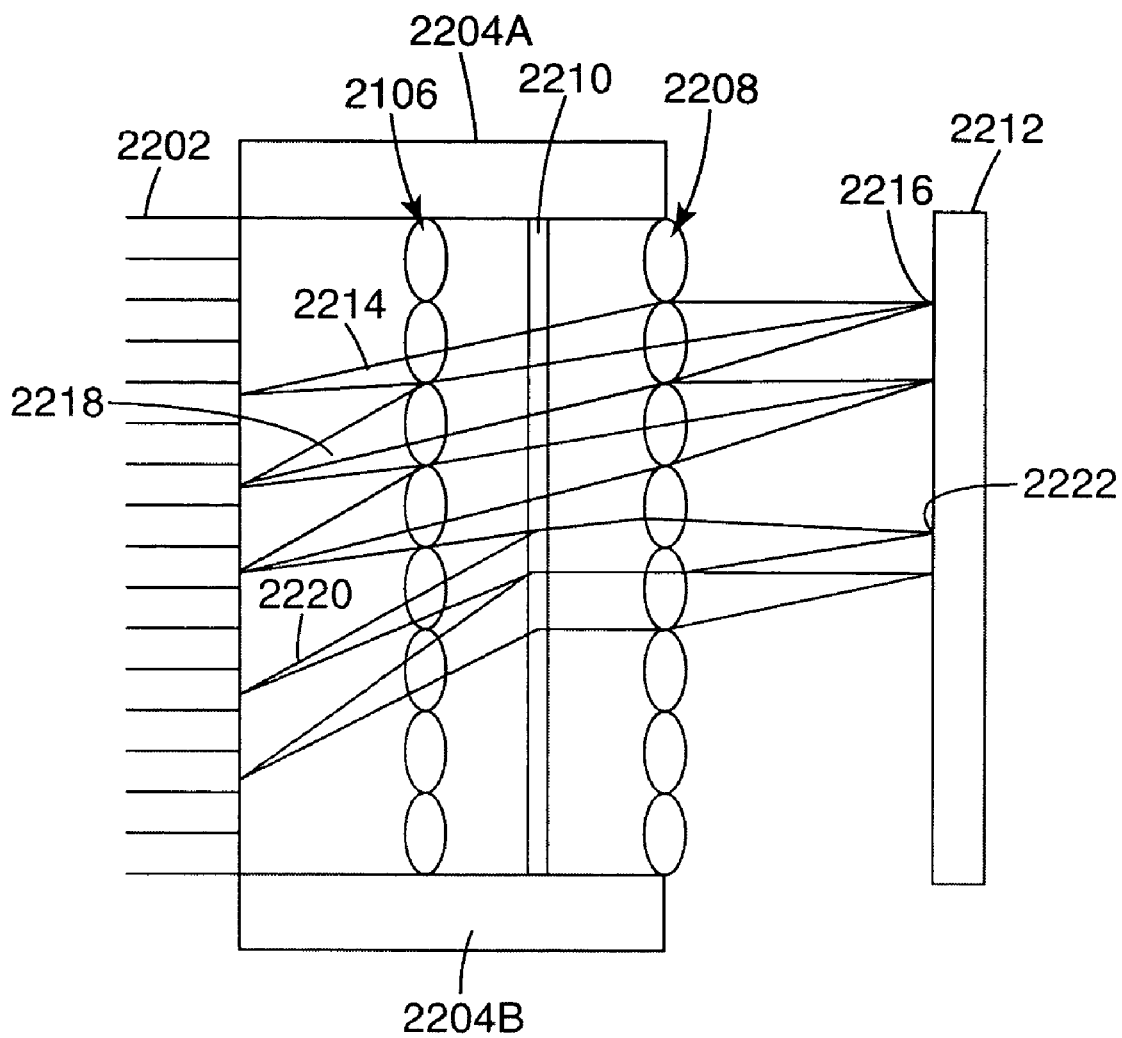
FIG. 28 shows a radiation modifying apparatus that utilizes a light valve to deflect radiation for creating a pattern and or to reduce high angles reaching a polarizer.

FIG. 28 shows a radiation modifying configuration that a deflecting light valve to create patterns and/or reduce radiation approach angles to a polarizer. A waveguide 2202 outputs radiation toward an optical element 2206, such as a lenslet array. As with the configuration of FIG. 26, to provide the effect of an infinite waveguide 2202, mirrors 2204A and 2204B may be included to reflect errant radiation back toward the optical element 2206. In this example, a second optical element 2208 such as a lenslet array is also included to further collimate light emanating from the first optical element 2206.

This configuration also includes a deflective light valve 2210 placed between the first optical element 2206 and the second optical element 2208. The deflective light valve 2210 may be a grating light valve or a digital mirror device. The deflective light valve 2210 has individually controllable cells so as to selective deflect light to create patterns as desired.

Several angles of radiation pathways as well as angles of non-radiation pathways are illustrated in FIG. 28 to demonstrate the deflection, and a smoothing is also illustrated. Non-radiation pathway 2214 extends from the small area between fibers of the waveguide 2202 from which no radiation emanates. As shown, this pathway 2214 extends to a point 2216 on the modifiable material 2212. However, rather than this point 2216 being exposed to no radiation, radiation pathway 2218 extends from a central region of a fiber to point 2216 such that the otherwise unexposed point 2216 receives radiation. However, in this example, the deflective light valve 2210 has been activated such that point 2224 receives radiation via pathways including pathway 2220 that has been deflected. The deflection redirects the radiation as desired, which can be used to create patterns in the radiation modifiable material 2212. Furthermore, the deflection decreases the angle of approach of the radiation which is useful where a polarizer (not shown in this figure) is located at a point between the optical element 2206 and the material 2212.

While the present invention has been described with a reference to exemplary preferred embodiments, the invention may be embodied in other specific forms without departing from the scope of the invention. Accordingly, it should be understood that the embodiments described and illustrated herein are only exemplary and should not be considered as limiting the scope of the present invention. Other variations and modifications may be made in accordance with the scope of the present invention.

We claim:

1. An irradiation apparatus, comprising:
a plurality of solid state radiation sources to generate radiation that modifies a first material;
a controller in electrical communication with the solid state radiation sources, wherein the controller individually and separately controls pulsing of each of the solid state radiation sources to generate individually and separately pulsed radiation;
a plurality of optical concentrators, wherein each concentrator receives pulsed radiation from one or more of the plurality of solid state radiation sources;
a plurality of optical waveguides, wherein each of the plurality of optical waveguides includes a first end and a second end, wherein each first end receives pulsed radiation from one or more of the plurality of optical concentrators; and
a support structure to stabilize at least a first portion of the second ends of the plurality of optical waveguides.

2. The irradiation apparatus of claim 1, wherein the controller causes pulsed radiation at a frequency of below one kilohertz.

3. The irradiation apparatus of claim 1, wherein the solid state radiation sources are LED dies and wherein the controller comprises an LED sign controller.

4. The irradiation apparatus of claim 1, wherein the controller causes pulse radiation at a frequency between one kilohertz and one megahertz.

5. The irradiation apparatus of claim 4, wherein the controller comprises a computer controlled digital signal generator in communication with a solid state switch array.

6. The irradiation apparatus of claim 1, wherein the controller causes a pulsed radiation at a frequency in excess of one megahertz.

7. The irradiation apparatus of claim 6, wherein the controller comprises a pulse generator in communication with a solid state switch array.

8. The irradiation apparatus of claim 1, further comprising an optical element in the path of the pulsed radiation.

9. An irradiation system, comprising:
   a solid state radiation source, comprising
      a plurality of LED dies to generate radiation that modifies a radiation modifiable chemical formulation;
      a controller electrically connected to the plurality of LED dies that causes the LED dies to produce pulsed radiation;
      a plurality of optical concentrators that are reflective optical couplers, wherein each concentrator receives the pulsed radiation from one or more of the LED dies and alters the path of the pulsed radiation;
      a plurality of optical fibers, wherein each of the plurality of optical fibers includes a first end and a second end, wherein each first end receives concentrated pulsed radiation from one or more of the plurality of optical concentrators including receiving pulsed radiation that is outside of the acceptance angle of the optical fibers when emanating from the LED dies but is inside the acceptance angle of the optical fibers after having the path altered by the optical concentrators; and
   a substrate to support the radiation modifiable chemical formulation.

10. The irradiation apparatus of claim 9, wherein the controller causes pulsed radiation with a frequency less than one kilohertz.

11. The irradiation apparatus of claim 9, wherein the controller causes pulsed radiation with a frequency between one kilohertz and one megahertz.

12. The irradiation apparatus of claim 9, wherein the controller causes pulsed radiation with a frequency greater than one megahertz.

13. The irradiation apparatus of claim 9, wherein the radiation modifiable chemical formulation is cured by the application of the pulsed radiation.

14. The irradiation apparatus of claim 13, wherein the radiation modifiable chemical formulation is cured by the creation of free radicals due to the pulsed radiation.

* * * * *

UNITED STATES PATENT AND TRADEMARK OFFICE
CERTIFICATE OF CORRECTION

PATENT NO. : 7,202,489 B2 Page 1 of 1
APPLICATION NO. : 10/869235
DATED : April 10, 2007
INVENTOR(S) : Francis M. Aguirre It is certified that error appears in the above-identified patent and that said Letters Patent is hereby corrected as shown below:

Page 2
Column 2 (Other Publications)
Line 16, delete "Sep.1," and insert in place thereof -- Mar. 1 --.

Column 9
Line 16, delete "6.5cm" and insert in place thereof -- $6.5cm^2$ --.

Column 16
Line 59, delete "FIG. 11B" and insert in place thereof -- FIG. 1B --.

Signed and Sealed this

Nineteenth Day of June, 2007

JON W. DUDAS
*Director of the United States Patent and Trademark Office*